US011071530B2

(12) United States Patent
Wang et al.

(10) Patent No.: US 11,071,530 B2
(45) Date of Patent: Jul. 27, 2021

(54) NEEDLE SYSTEM RESTRICTOR

(71) Applicant: Gyrus ACMI, Inc., Southborough, MA (US)

(72) Inventors: Huisun Wang, Maple Grove, MN (US); Eric Stender, Champlin, MN (US); Kester J. Batchelor, Mound, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 504 days.

(21) Appl. No.: 15/937,440

(22) Filed: Mar. 27, 2018

(65) Prior Publication Data

US 2019/0298320 A1    Oct. 3, 2019

(51) Int. Cl.
*A61B 10/02* (2006.01)
*A61M 1/00* (2006.01)
*A61B 10/04* (2006.01)

(52) U.S. Cl.
CPC ....... *A61B 10/0283* (2013.01); *A61M 1/0049* (2013.01); *A61B 2010/045* (2013.01)

(58) Field of Classification Search
CPC .......... A61B 10/0283; A61B 2010/045; A61B 5/150221; A61B 1/00068; F16K 7/07; A61M 1/0049
USPC ....................................................... 600/566
See application file for complete search history.

(56) References Cited

U.S. PATENT DOCUMENTS

| 2,524,764 | A | * | 10/1950 | Burke ................... F16K 15/147 |
| | | | | 137/217 |
| 3,565,079 | A | | 2/1971 | Jackson |
| 4,458,721 | A | | 7/1984 | Yie et al. |
| 7,163,525 | B2 | | 1/2007 | Franer |
| 9,291,284 | B2 | | 3/2016 | Penterman et al. |
| 9,326,755 | B2 | * | 5/2016 | Fiebig ................ A61B 10/0275 |
| 2008/0300618 | A1 | | 12/2008 | Gertner |
| 2012/0330342 | A1 | | 12/2012 | Jones et al. |
| 2016/0367231 | A1 | | 12/2016 | Uemichi et al. |

FOREIGN PATENT DOCUMENTS

| WO | WO93018324 A1 | 9/1993 | |
| WO | WO2015060762 A1 | 4/2015 | |
| WO | WO-2016153770 A1 * | 9/2016 | ......... A61B 10/0266 |
| WO | WO-2018174882 A1 * | 9/2018 | ...... A61M 25/10186 |

* cited by examiner

*Primary Examiner* — David J. McCrosky
*Assistant Examiner* — Chanel J Jhin
(74) *Attorney, Agent, or Firm* — Schwegman Lundberg & Woessner, P.A.

(57) ABSTRACT

A needle system includes a handle, a needle slider partially positioned in the handle, and a needle connected to and extending away from the needle slider. A restrictor is disposed in the needle. The restrictor is configured to inhibit passage of a sample through the needle slider.

20 Claims, 16 Drawing Sheets

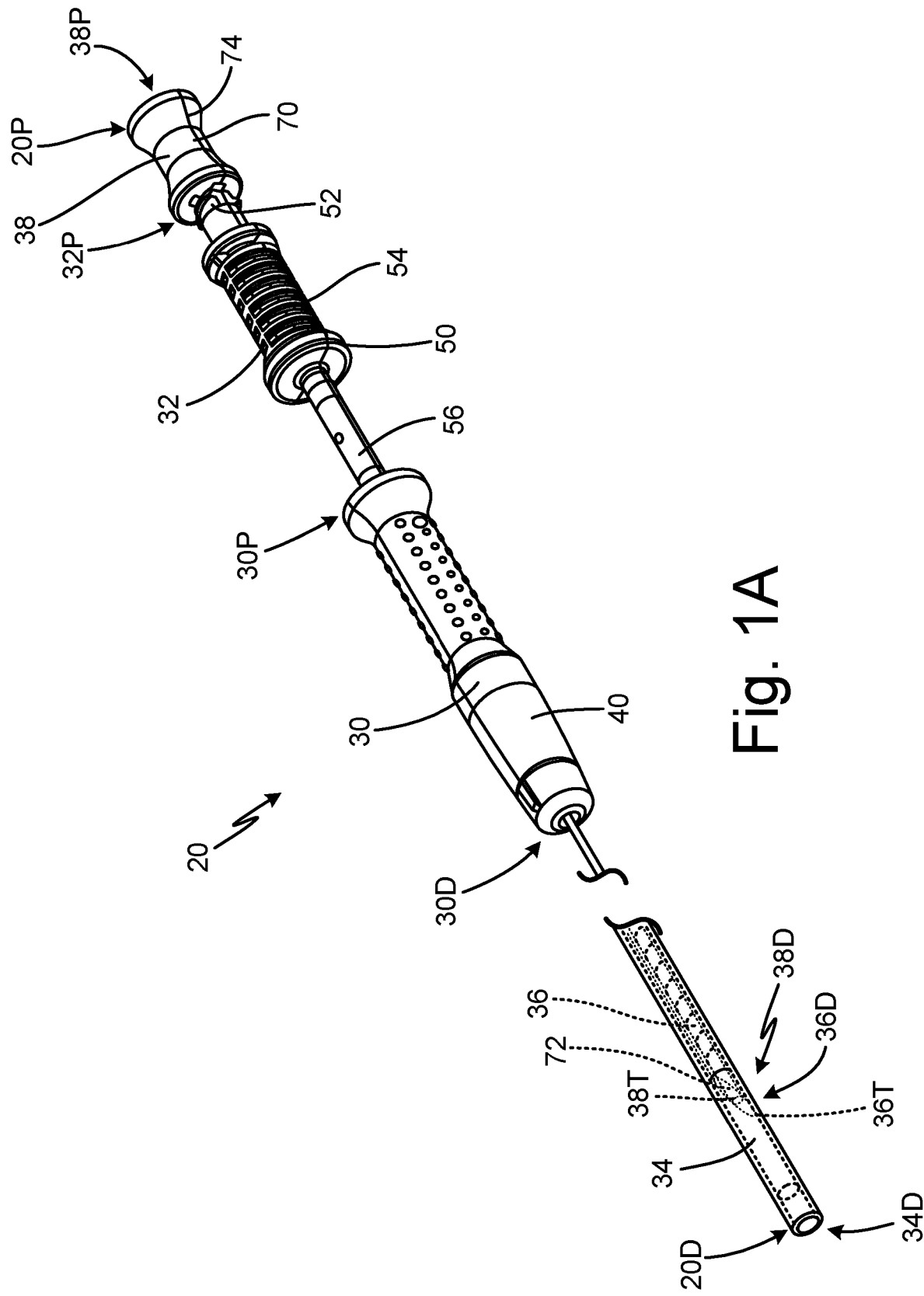

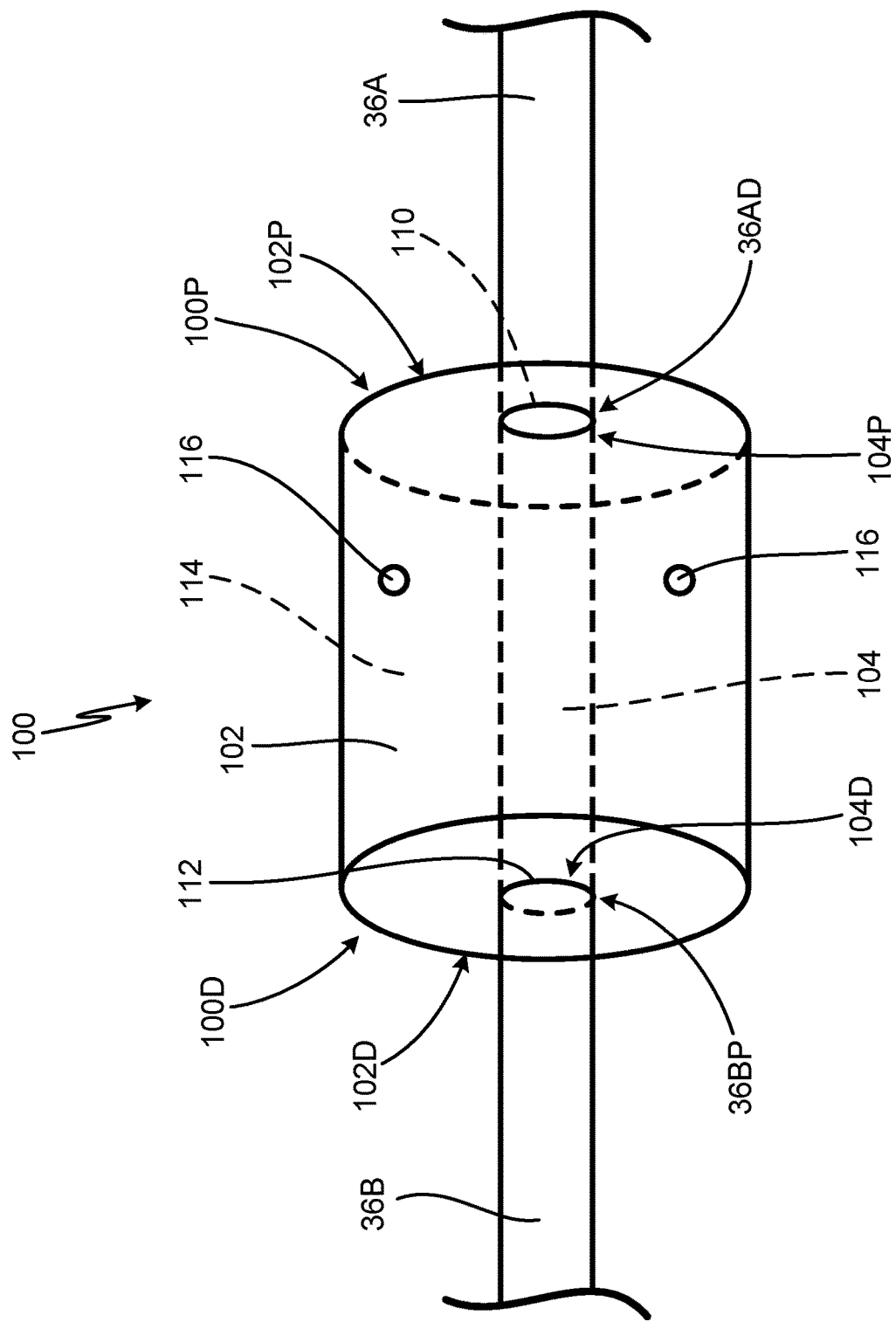

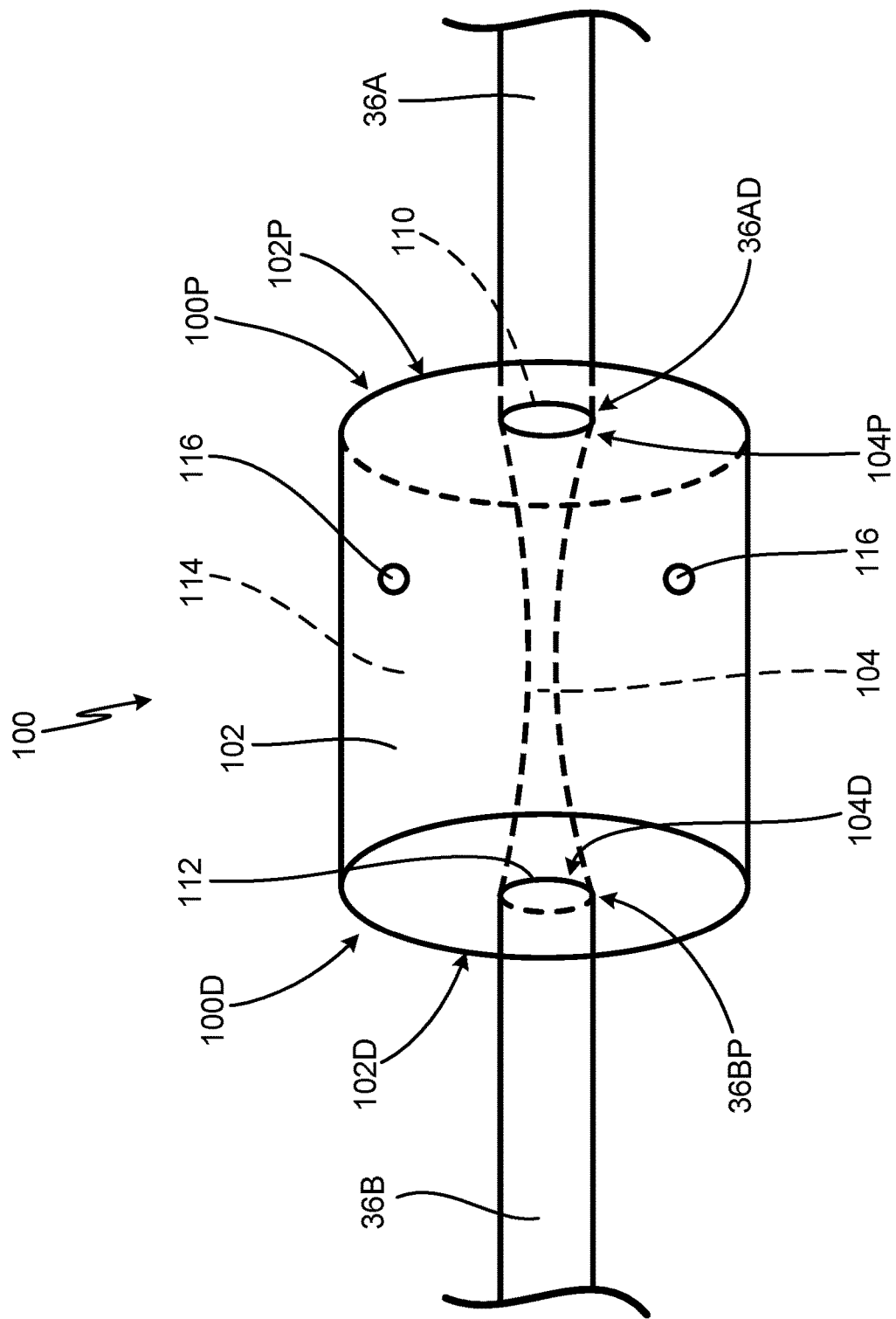

NEEDLE SYSTEM RESTRICTOR

BACKGROUND

The present disclosure relates to a needle system, and in particular, to a restrictor for a needle system.

Endobronchial ultrasound (EBUS) is a diagnostic or staging procedure for lung cancer, lung infections, and other diseases causing enlarged lymph nodes or masses in the chest. EBUS uses an endoscope with ultrasound to visualize the airways, blood vessels, lungs, and lymph nodes in the tracheal and bronchial tree of a patient. Trans-bronchial needle aspiration (TBNA) can be used to perform a biopsy of lesions or lymph nodes within the tracheal and bronchial tree. Endobronchial ultrasound trans-bronchial needle aspiration (EBUS-TBNA) uses ultrasound to visualize the airways, blood vessels, lungs, and lymph nodes in the tracheal and bronchial tree of a patient to perfom a biopsy of lesions or lymph nodes within the tracheal and bronchial tree.

During an EBUS-TBNA procedure, an endoscope is inserted into a patient with the head of the endoscope positioned next to a lesion or lymph node from which a sample is to be taken. The endoscope includes a channel through which a needle system can be guided. The needle system includes a sheath connected to a handle. A needle is positioned in the sheath and connected to a needle slider. The needle slider is partially positioned in and movable in the handle. The needle slider can be moved from a retracted position where the needle is held in the sheath to an advanced position where the needle is advanced out of the sheath. In the advanced position, the needle can puncture the lesion or lymph node from which a biological sample is to be taken. A syringe can be connected to an aspiration port on the needle slider and suction can be applied to the needle system to create a vacuum in the needle system. The needle is then moved backwards and forwards in the lesion or lymph node with the needle slider to aspirate a biological sample from the lesion or lymph node into the needle. The needle system is removed from the endoscope and the biological sample is pushed out of the needle to be used for biopsy analysis.

In some existing needle systems, the vacuum generated by the syringe can draw the collected biological sample from the lesion or lymph node into the syringe. This renders the biological sample unsuitable for biopsy analysis.

SUMMARY

A needle system includes a handle, a needle slider partially positioned in the handle, and a needle connected to and extending away from the needle slider. A restrictor is disposed in the needle. The restrictor is configured to inhibit passage of a sample through the needle slider.

A needle system includes a needle slider having an aspiration port on a proximal end of the needle slider, a needle connected to and extending away from the needle slider, and a syringe attached to the aspiration port of the needle slider. A restrictor is disposed in the needle. The restrictor is configured to deform and inhibit passage of a sample through the needle slider when a vacuum is drawn by the syringe.

A restrictor includes a hollow housing with a proximal end having a proximal port and a distal end having a distal port, and a flexible member extending from the proximal port to the distal port of the hollow housing. The housing is configured to be positioned around a needle. The flexible member is configured to deform when a vacuum is applied to the needle.

A method includes advancing a needle of the needle system out of a sheath of the needle system and into a biological sample. The needle system further includes a handle and a needle slider partially positioned in the handle. The sheath is secured in the handle and the needle is secured in the needle slider and extends through the sheath. A syringe is connected to an aspiration port of the needle slider of the needle system. A vacuum is created in the needle system with the syringe. A restrictor that is positioned in-line with the needle deforms under the vacuum in the needle system. The biological sample is aspirated into the needle of the needle system. The biological sample is inhibited, with the restrictor, from moving into the syringe.

BRIEF DESCRIPTION OF THE DRAWINGS

FIG. 1A is an isometric view of a needle system in a retracted position.

FIG. 6A is a perspective view of a restrictor in a natural state.

FIG. 6B is a perspective view of the restrictor of FIG. 6A in a deformed state.

DETAILED DESCRIPTION

Needle System 20 (FIGS. 1A-5)

Figure 1B:
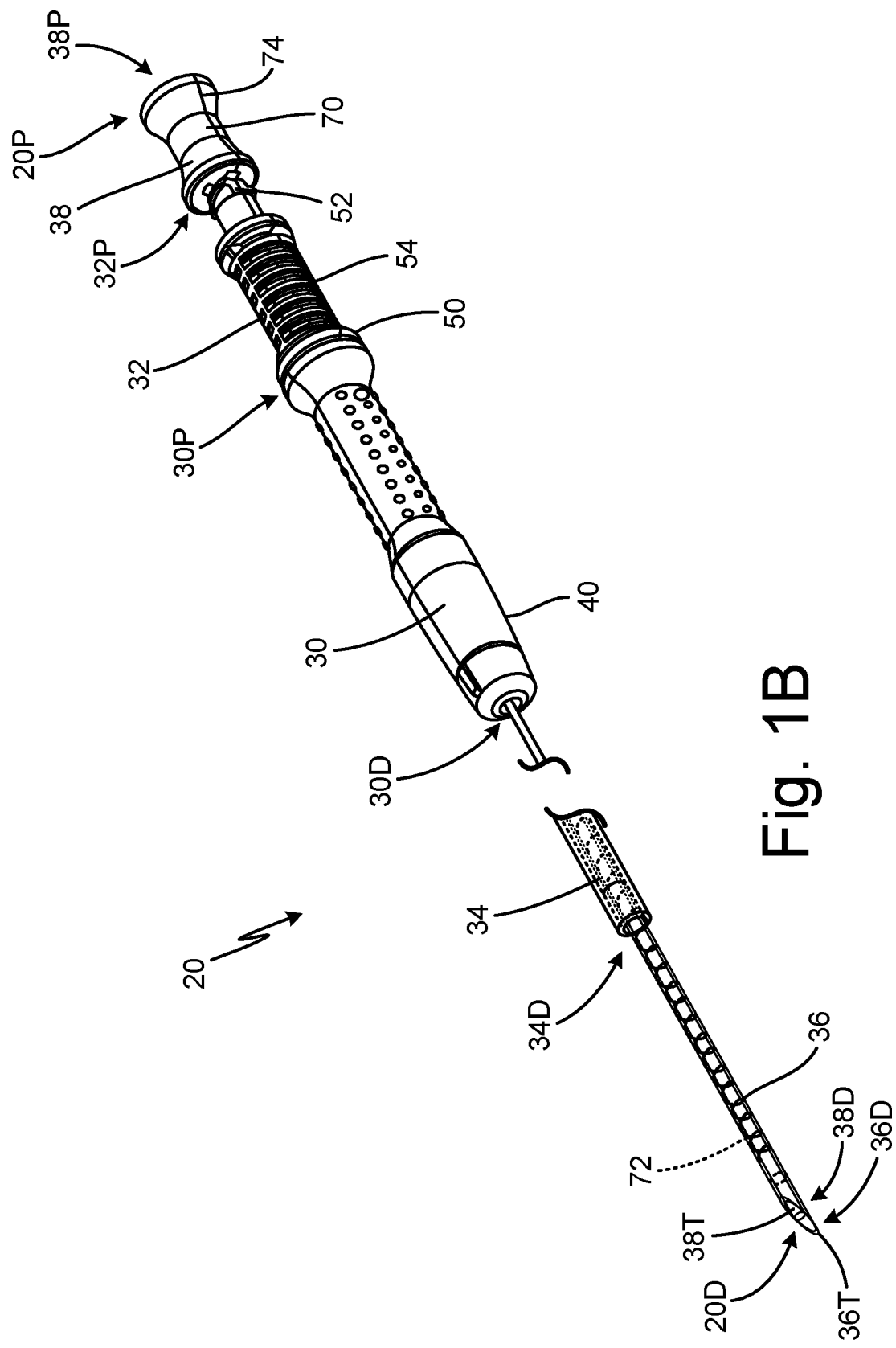
FIG. 1B is an isometric view of the needle system in an advanced position.
Figure 2A:
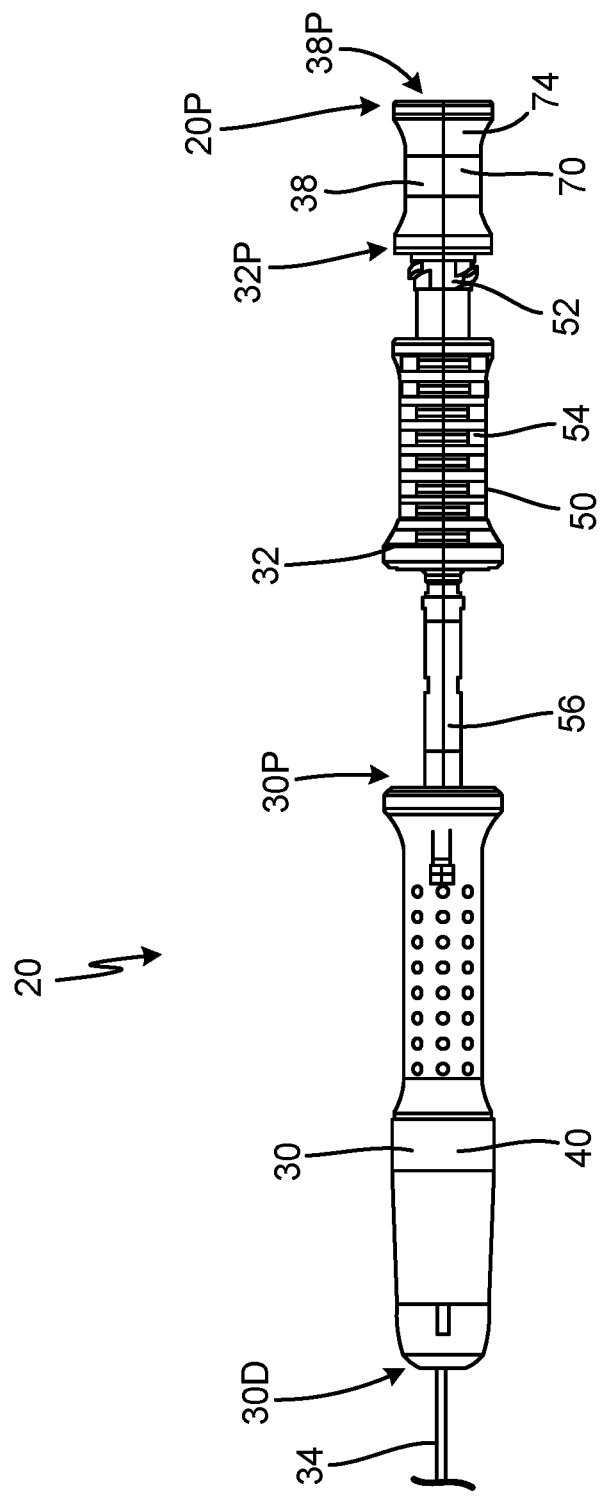
FIG. 2A is a side view of the needle system in the retracted position.
Figure 2B:
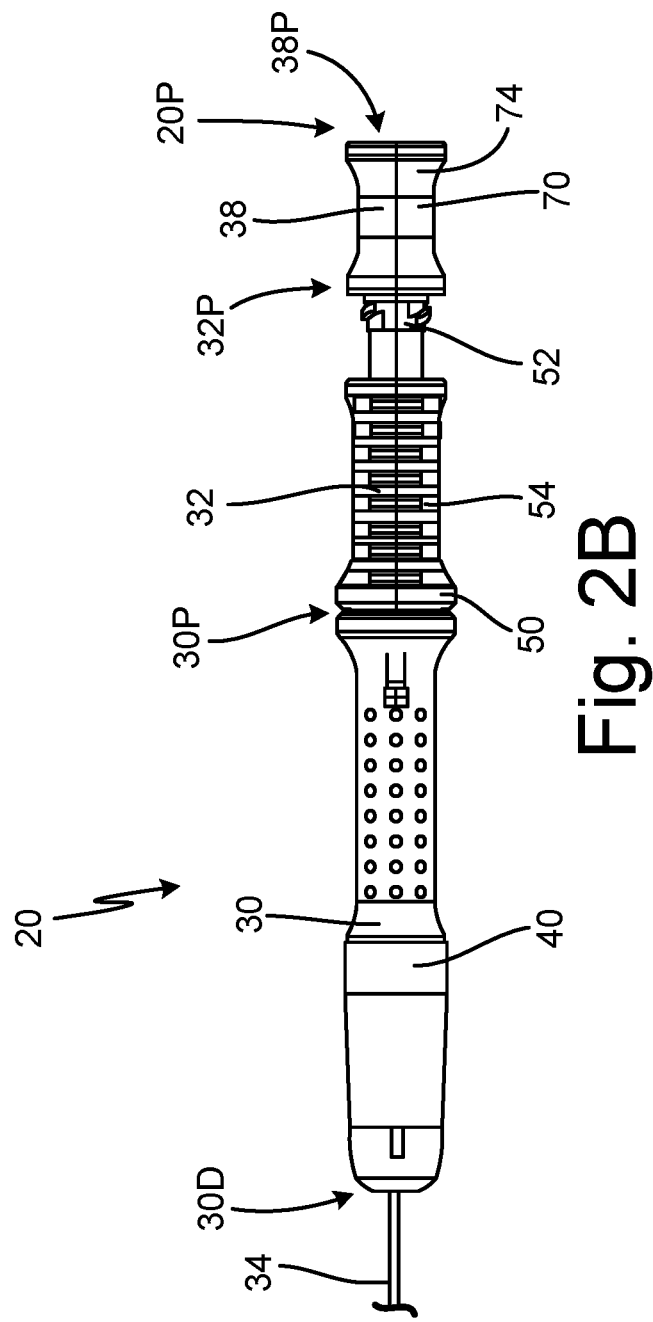
FIG. 2B is a side view of the needle system in the advanced position.
Figure 3:
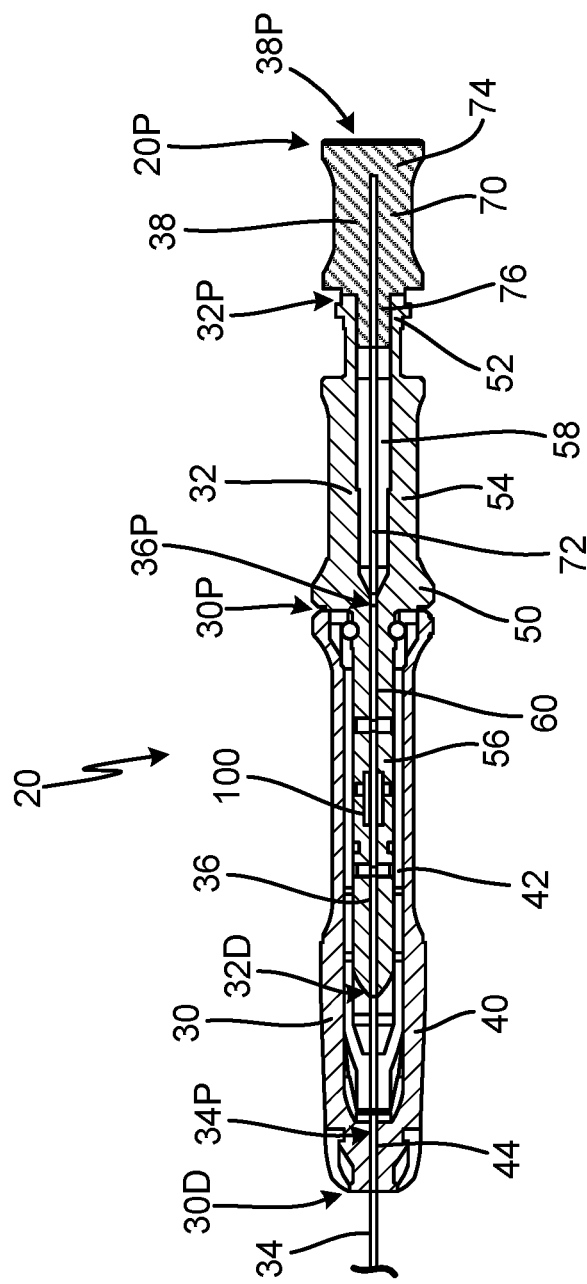
FIG. 3 is a cross-sectional view of the needle system in the advanced position.
Figure 4:
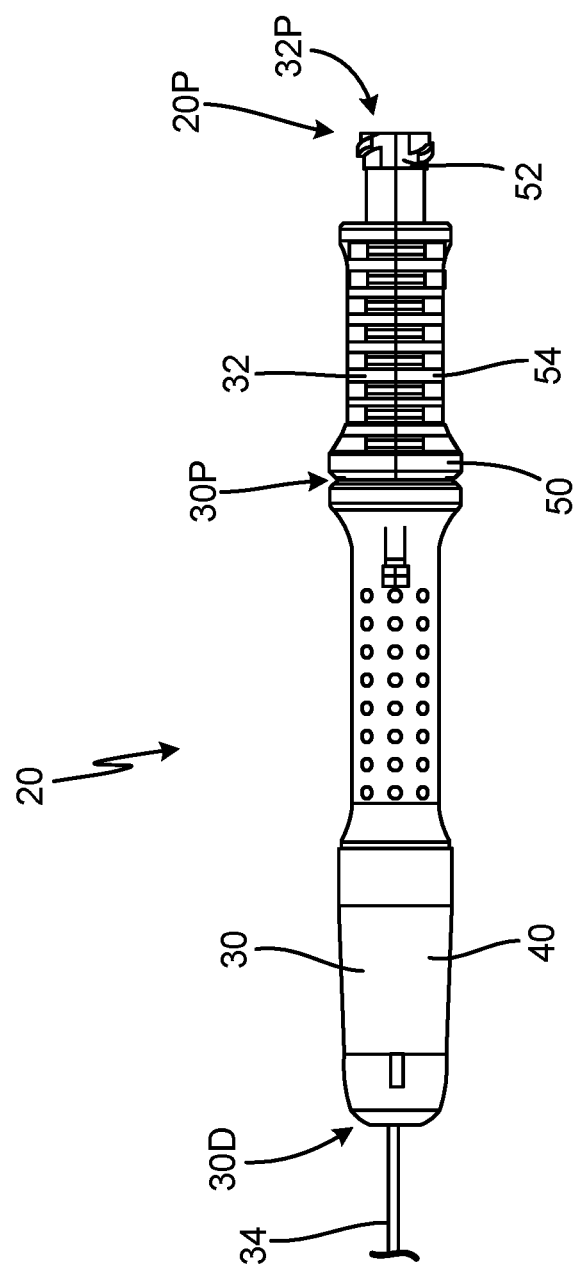
FIG. 4 is a side view of the needle system when a stylet has been removed.
Figure 5:
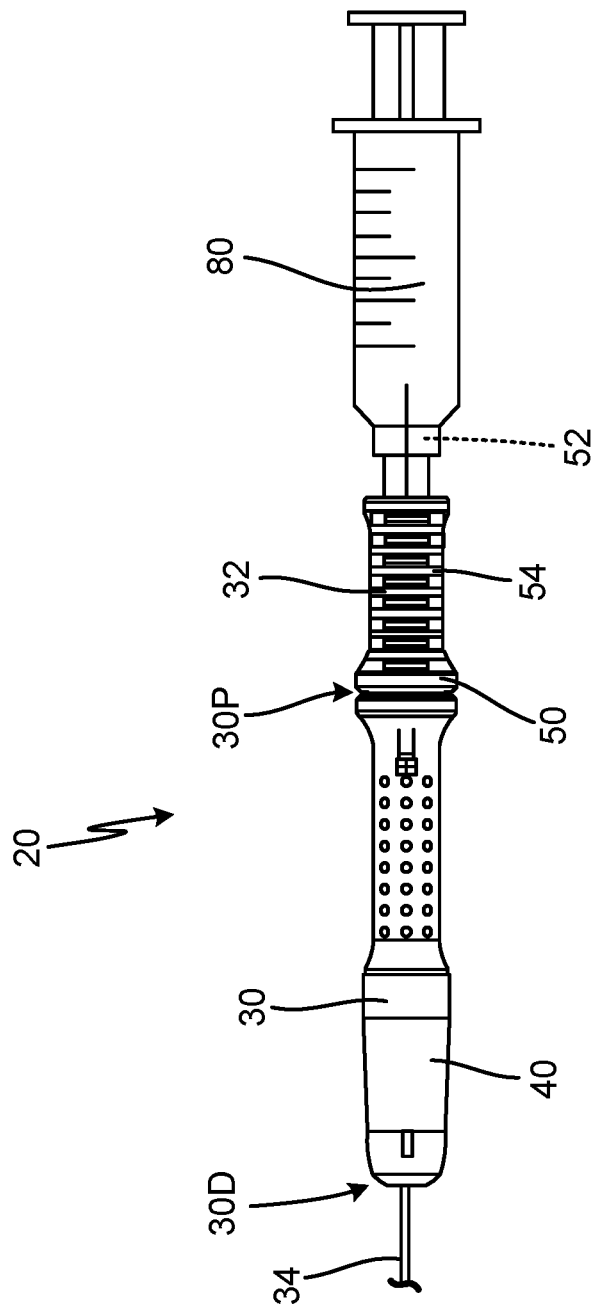
FIG. 5 is a side view of the needle system with a syringe attached.

FIG. 1A is an isometric view of needle system 20 in a retracted position. FIG. 1B is an isometric view of needle system 20 in an advanced position. FIGS. 1A-1B show an enlarged view of distal end 20D of needle system 20 for clarity. FIG. 2A is a side view of needle system 20 in the retracted position. FIG. 2B is a side view of needle system 20 in the advanced position. FIG. 3 is a cross-sectional view of needle system 20 in the advanced position. FIG. 4 is a side view of needle system 20 when stylet 38 has been removed. FIG. 5 is a side view of needle system 20 with syringe 80 attached. FIGS. 2B-5 do not show distal end 20D of needle system 20. FIGS. 1A-5 will be discussed together. Needle system 20 includes handle 30, needle slider 32, sheath 34, needle 36, and stylet 38. Handle 30 includes housing 40, first bore 42, and second bore 44. Needle slider 32 includes housing 50, aspiration port 52, grip 54, shaft 56, first bore 58, and second bore 60. Stylet 38 includes knob 70, wire 72, head portion 74, and neck portion 76. FIG. 5 also shows syringe 80, and FIG. 3 shows restrictor 100.

Needle system 20 includes proximal end 20P and distal end 20D. Needle system 20 includes handle 30 forming a body portion that can be gripped by a user while using needle system 20. Handle 30 includes proximal end 30P and distal end 30D. Needle slider 32 is partially positioned in and movable within handle 30. Needle slider 32 includes proximal end 32P and distal end 32D (FIG. 3). Sheath 34 is connected to distal end 30D of handle 30 and extends axially away from handle 30. Sheath 34 includes proximal end 34P (FIG. 3) and distal end 34D. Needle 36 is connected to distal end 32D of needle slider 32 and extends axially away from needle slider 32. Needle 36 includes proximal end 36P (FIG. 3), distal end 36D, and tip 36T. Needle 36 extends through and is coaxial with sheath 34. Stylet 38 is positioned at proximal end 32P of needle slider 32 and extends through needle slider 32 and needle 36. Stylet 38 includes proximal end 38P, distal end 38D, and tip 38T.

Needle system 20 can be moved between a retracted position and an advanced position via manual actuation of needle slider 32. Needle system 20 is shown in the retracted position in FIGS. 1A and 2A. In the retracted position, tip 36T of needle 36 is positioned within distal end 34D of sheath 34. Needle system 20 is shown in the advanced position in FIGS. 1B and 2B-5. In the advanced position, tip 36T of needle 36 is positioned outside of sheath 34 beyond distal end 34D of sheath 34. Needle system 20 is moved between the retracted position and the advanced position by moving needle slider 32 into and out of handle 30. As needle slider 32 is pushed into handle 30, the tip of needle 36 is advanced outside of sheath 34. As needle slider 32 is pulled out of handle 30, the tip of needle 36 is retracted into sheath 34.

As shown in FIG. 3, handle 30 includes housing 40 that forms the body of handle 30. Handle 30 also includes first bore 42 and second bore 44. First bore 42 extends through proximal end 30P of handle 30. First bore 42 is cylindrically shaped in the embodiment shown, but can have any suitable shape in alternate embodiments. Second bore 44 extends through distal end 30D of handle 30. Second bore 44 is cylindrically shaped in the embodiment shown, but can have any suitable shape in alternate embodiments. First bore 42 has a diameter that is greater than a diameter of second bore 44.

Housing 50, which includes aspiration port 52, grip 54, and shaft 56, forms the body of needle slider 32. Aspiration port 52 is situated at proximal end 32P of needle slider 32, grip 54 is situated between aspiration port 52 and shaft 56, and shaft 56 is situated at distal end 32D of needle slider 32. Needle slider 32 includes first bore 58 and second bore 60. First bore 58 extends through aspiration port 52 and grip 54 of needle slider 32. First bore 58 is cylindrically shaped in the embodiment shown, but can have any suitable shape in alternate embodiments. Second bore 60 extends through shaft 56 of needle slider 32. Second bore 60 is cylindrically shaped in the embodiment shown, but can have any suitable shape in alternate embodiments. First bore 58 has a diameter that is greater than a diameter of second bore 60.

Shaft 56 of needle slider 32 is positioned in and movable in first bore 42 of handle 30. As shown in FIGS. 1A and 2A, when needle system 20 is in a retracted position, a majority of shaft 56 of needle slider 32 will not be positioned in first bore 42 of handle 30. As shown in FIGS. 1B and 2B-5, when needle system 20 is in an advanced position, the entirety of shaft 56 of needle slider 32 is positioned in first bore 42 of handle 30.

Sheath 34 is a tube that extends away from distal end 30D of handle 30. Sheath 34 is made of a polymeric material in the embodiment shown. In alternate embodiments, sheath 34 can be made of other suitable materials. Proximal end 34P of sheath 34 is positioned in and secured in second bore 44 of handle 30. Needle 36 is a tube that extends away from distal end 32D of needle slider 32. Needle 36 has tip 36T on distal end 36D. Needle 36 is made of a metal, such as stainless steel, in the embodiment shown. In alternate embodiments, needle 36 can be made of other suitable materials. Proximal end 36P of needle 36 is positioned in and secured in second bore 60 of needle slider 32.

Stylet 38 includes knob 70 and wire 72. Knob 70 forms a body of stylet 38. Knob 70 includes head portion 74 and neck portion 76. Head portion 74 abuts aspiration port 52 of needle slider 32. Neck portion 76 is positioned in first bore 58 of needle slider 32 when stylet 38 is positioned in needle system 20. Wire 72 is positioned in and extends away from knob 70. Wire 72 extends through first bore 58 and second bore 60 of needle slider 32 and through needle 36. Wire 72 of stylet 38 is coaxial with needle 36. Tip 38T of stylet 38 is positioned in tip 36T of needle 36 when stylet 38 is positioned in needle system 20. Stylet 38 can be removed from needle system 20 by pulling knob 70 away from needle slider 32 and pulling wire 72 out of needle system 20.

Needle system 20 can be used as a single-use aspiration needle for taking biopsies. For example, needle system 20 can be used during trans-bronchial needle aspiration (TBNA) to perform a biopsy of a lesion or a lymph node in the tracheal and bronchial tree of a patient. More specifically, needle system 20 can be used during endobronchial ultrasound trans-bronchial needle aspiration (EBUS-TBNA). During an EBUS-TBNA procedure, an endoscope with ultrasound capabilities is used to visualize the airways, blood vessels, lungs, and lymph nodes in the tracheal and bronchial tree.

Once the endoscope is positioned adjacent to a lesion or a lymph node from which a biological sample is to be collected, sheath 34 of needle system 20 can be inserted through a channel in the endoscope. Handle 30 can be grasped by a user and used to maneuver sheath 34 into position in the endoscope. Needle 36 and wire 72 of stylet 38 provide structural support to sheath 34 as it is inserted into the endoscope, while also allowing sheath 34 to remain flexible. Needle system 20 is in a retracted position, as shown in FIGS. 1A and 2A, when sheath 34 is inserted through the endoscope to ensure that tip 36T of needle 36 does not puncture the endoscope.

After sheath 34 of needle system 20 is inserted into the endoscope, needle system 20 is moved to an advanced position, as shown in FIGS. 1B and 2B-5. Needle slider 32 is pushed into handle 30 of needle system 20 to advance the tip of needle 36 into the target lesion or lymph node. Stylet 38 is then removed from needle system 20, as shown in FIG. 4. When stylet 38 is removed, aspiration port 52 of needle slider 32 forms proximal end 20P of needle system 20, and first bore 58 of needle slider 32 is exposed.

Syringe 80 is attached to proximal end 32P of needle slider 32, as shown in FIG. 5. Syringe 80 has luer fittings that mate to luer fittings on proximal end 32P of needle slider 32. Syringe 80 is used to create a vacuum in needle system 20. First bore 58 of needle slider 32, second bore 60 of needle slider 32, and a lumen of needle 36 form a flow path through needle system 20. A plunger of syringe 80 is pulled to apply suction to needle system 20, creating a vacuum in the flow path extending through first bore 58 of needle slider 32, second bore 60 of needle slider 32, and a lumen of needle 36.

After a vacuum has been applied with syringe 80, needle slider 32 is moved into and out of handle 30, moving the tip of needle 36 backwards and forwards within the lesion or lymph node. A biological sample from the lesion or lymph node will be aspirated into needle 36 via the vacuum supplied by syringe 80 and the movement of needle slider 32. The biological sample that is aspirated into needle system 20 is drawn under suction into the lumen of needle 36, second bore 60 of needle slider 32, and first bore 58 of needle slider 32. After a biological sample has been aspirated into needle 36, syringe 80 is removed from proximal end 32P of needle slider 32. Needle system 20 is then removed from the endoscope and the biological sample is removed from needle 36 for biopsy analysis.

One challenge that is faced in using needle system 20 is preventing the aspirated biological sample from entering syringe 80. If the biological sample enters syringe 80, it is unsuitable for use in a biopsy analysis. This would require a second needle system 20 to be inserted into the endoscope to collect a new sample for conducting the biopsy analysis. Restrictor 100 is placed in-line with needle 36 and is positioned in shaft 56 of needle slider 32 to prevent biological material from being drawn into syringe 80. Restrictor 100 can be seen in FIG. 3. Restrictor 100 has a housing and a flexible member that can be deformed when a vacuum is applied to needle system 20 with syringe 80.

As will be discussed below with reference to FIGS. 6A-12, in its natural state, the flexible member of restrictor 100 (or of restrictors 200, 300, 400, or 500) will have the same diameter as needle 36, allowing needle 72 of stylet 38 to pass through restrictor 100. When a vacuum is applied to needle system 20, the flexible member of restrictor 100 will deform so that a diameter of the center of a flexible member is smaller than a diameter of needle 36. This reduced diameter will inhibit the biological material from moving through restrictor 100 and needle slider 32 into syringe 80. Restrictor 100 acts as an internal nozzle and/or phase separator, as it allows fluid to pass through (thus allowing syringe 80 to create a vacuum, or partial vacuum, in needle system 20) but inhibits solid material from passing through (the aspirated biological sample).

Restrictor 100 (FIGS. 6A-6B)

FIG. 6A is a perspective view of restrictor 100 in a natural state. FIG. 6B is a perspective view of restrictor 100 in a deformed state. FIGS. 6A-6B show restrictor 100 in-line with needle 36. Needle 36 includes first needle portion 36A and second needle portion 36B. Restrictor 100 includes housing 102 and flexible member 104. Housing 102 includes proximal port 110, distal port 112, cavity 114, and vent holes 116.

Restrictor 100 is placed in-line with needle 36. Needle 36 includes first needle portion 36A and second needle portion 36B. FIGS. 6A-6B show distal end 36AD of first needle portion 36A and proximal end 36BP of second needle portion 36B. Restrictor 100 includes proximal end 100P and distal end 100D. First needle portion 36A of needle 36 is positioned on proximal end 100P of restrictor 100, and second needle portion 36B of needle 36 is positioned on distal end 100D of restrictor 100. Restrictor 100 includes housing 102 that forms a hollow body portion of restrictor 100. Housing 102 has proximal end 102P and distal end 102D. Flexible member 104 is a hollow tube that extends through an interior of housing 102 from proximal end 102P to distal end 102D. Flexible member 104 has proximal end 104P and distal end 104D.

Housing 102 may be cylindrically shaped and has proximal port 110 on proximal end 102P and distal port 112 on distal end 102D. Proximal port 110 and distal port 112 are circular openings in proximal end 102P and distal end 102D, respectively, of housing 102. Housing 102 further includes cavity 114 formed in an interior of housing 102. Vent holes 116 extend through housing 102 to connect cavity 114 to an exterior of housing 102. The embodiment shown in FIGS. 6A-6B shows two vent holes 116, but alternate embodiments can include any suitable number of vent holes 116. Housing 102 is made of a rigid material. Housing 102 is made of metal, such as stainless steel in the embodiment shown, but can be made of any suitable rigid material in alternate embodiments. Housing 102 is positioned around needle 36 and can be affixed to needle 36. For example, housing 102 can be welded to needle 36. An inner diameter of proximal port 110 can be affixed to an outer diameter of distal end 36AD of first needle portion 36A, and an inner diameter of distal port 112 can be affixed to an outer diameter of proximal end 36BP of second needle portion 36B.

Flexible member 104 extends through housing 102. Flexible member 104 extends through cavity 114 of housing 102 from first port 110 to second port 112 of housing 102. Flexible member 104 is connected to needle 36 at proximal end 104P and at distal end 104D. Proximal end 104P of flexible member 104 is connected to distal end 36AD of first needle portion 36A, and distal end 104D of flexible member 104 is connected to proximal end 36BP of second needle portion 36B. As such, flexible member 104 is in-line with needle 36 and a flow path is formed through a lumen of needle 36 and a lumen of flexible member 104. Flexible member 104 is made of an elastic polymer, such as polyurethane or latex, in the embodiment shown, but can be made of any suitable flexible material in alternate embodiments.

As shown in FIG. 6A, when restrictor 100 is in its natural, un-deformed state, flexible member 104 has a cylindrical shape with a radially outer wall that extends straight from first port 110 to second port 112 of housing 102. In its natural, un-deformed state, an inner diameter of flexible member 104 is equal to an inner diameter of needle 36. As shown in FIG. 6B, when restrictor 100 is in its deformed state, flexible member 104 collapses inward so that the radially outer wall is curved inwards from first port 110 to second port 112 of housing 102. In its deformed state, an inner diameter of a center of flexible member 104 is smaller than the inner diameter of needle 36.

When a pressure in cavity 114 of housing 102 is greater than a pressure in the lumen of flexible member 104, flexible member 104 will deform. The pressure in cavity 114 is atmospheric pressure, as cavity 114 is in fluid communication with an ambient surrounding restrictor 100 through vent holes 116. In its natural state, the pressure in the lumen of flexible member 104 will be atmospheric pressure and flexible member 104 is un-deformed.

As shown in FIGS. 1A-5, a vacuum can be applied to needle 36 of needle system 20 with syringe 80. The vacuum is applied to the flow path extending through the lumen of needle 36 and the lumen of flexible member 104. This decreases the pressure in the lumen of flexible member 104 to less than the atmospheric pressure. The atmospheric pressure in cavity 114 of housing 102 will thus be greater than the pressure in the lumen of flexible member 104. The atmospheric pressure in cavity 114 of housing 102 will press on the outer wall of flexible member 104, causing flexible member 104 to deform. Flexible member 104 of restrictor 100 thus deforms when a vacuum is applied to needle 36.

The amount of deformation of flexible member 104 can be controlled by controlling the vacuum that is applied to needle 36. Applying a small vacuum will create a small deformation where the inner diameter of flexible member 104 will be slightly smaller than the inner diameter of needle 36. Applying a large vacuum will create a large deformation where the inner diameter of flexible member 104 will be much smaller than the inner diameter of needle 36.

When flexible member 104 is in the natural, un-deformed state, both fluid and solid material can move through restrictor 100. When flexible member 104 of restrictor 100 deforms, fluid can move through restrictor 100 but solid material will be inhibited from moving through restrictor 100. Allowing fluid to move through restrictor 100 allows a vacuum to be created and maintained in restrictor 100. When flexible member 104 of restrictor 100 is deformed, the inner diameter of flexible member 104 of restrictor 100 will be smaller than the inner diameter of needle 36. The smaller diameter of flexible member 104 of restrictor 100 will inhibit solid material, such as the biological sample that is aspirated into needle 36, from moving through restrictor 100. Thus, solid material, such as the biological material that is aspirated into needle 36, is inhibited from being drawn into syringe 80.

Figure 7:
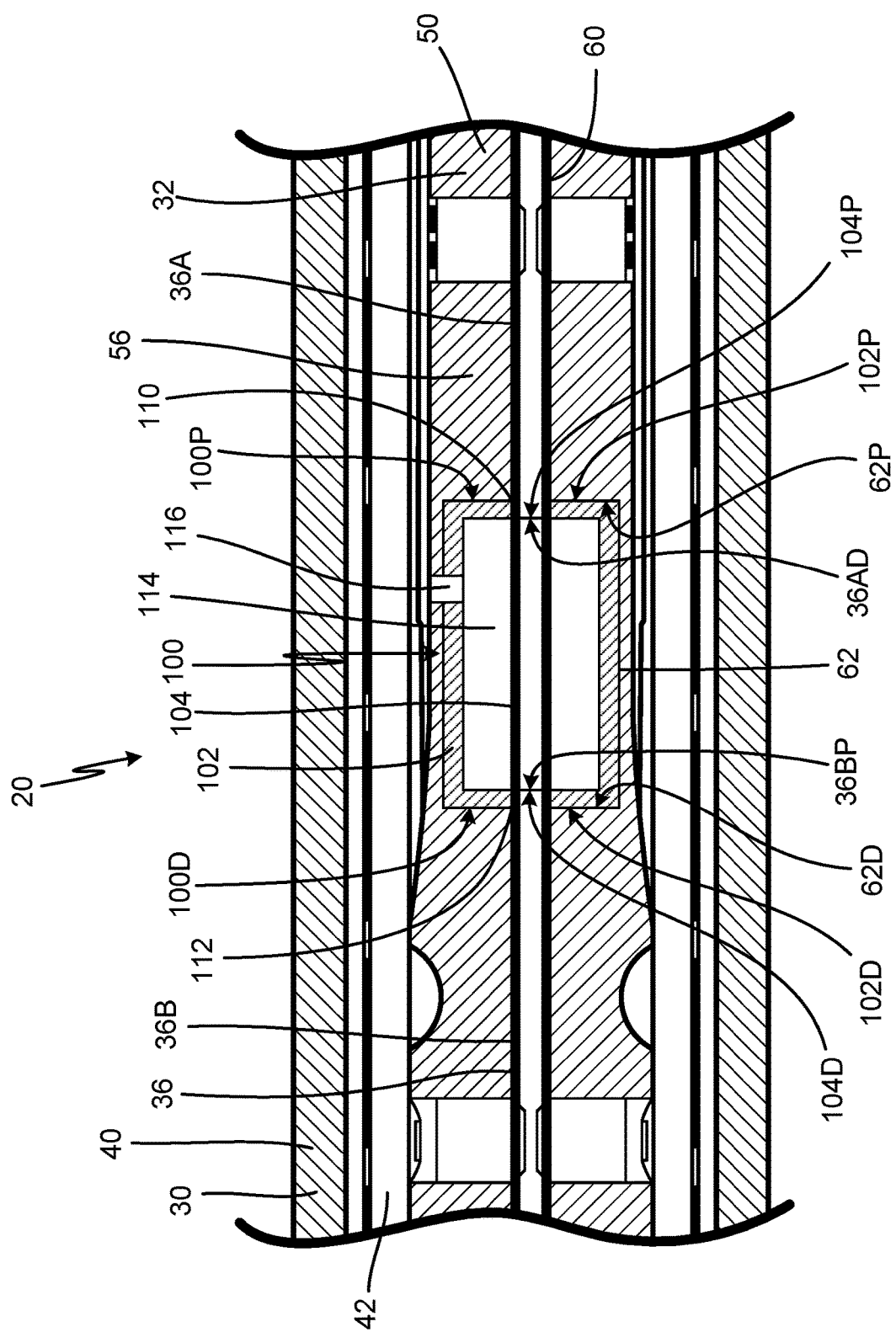
FIG. 7 is a cross-sectional view of the restrictor where a housing of the restrictor is positioned in a needle slider of the needle system.
Figure 8:
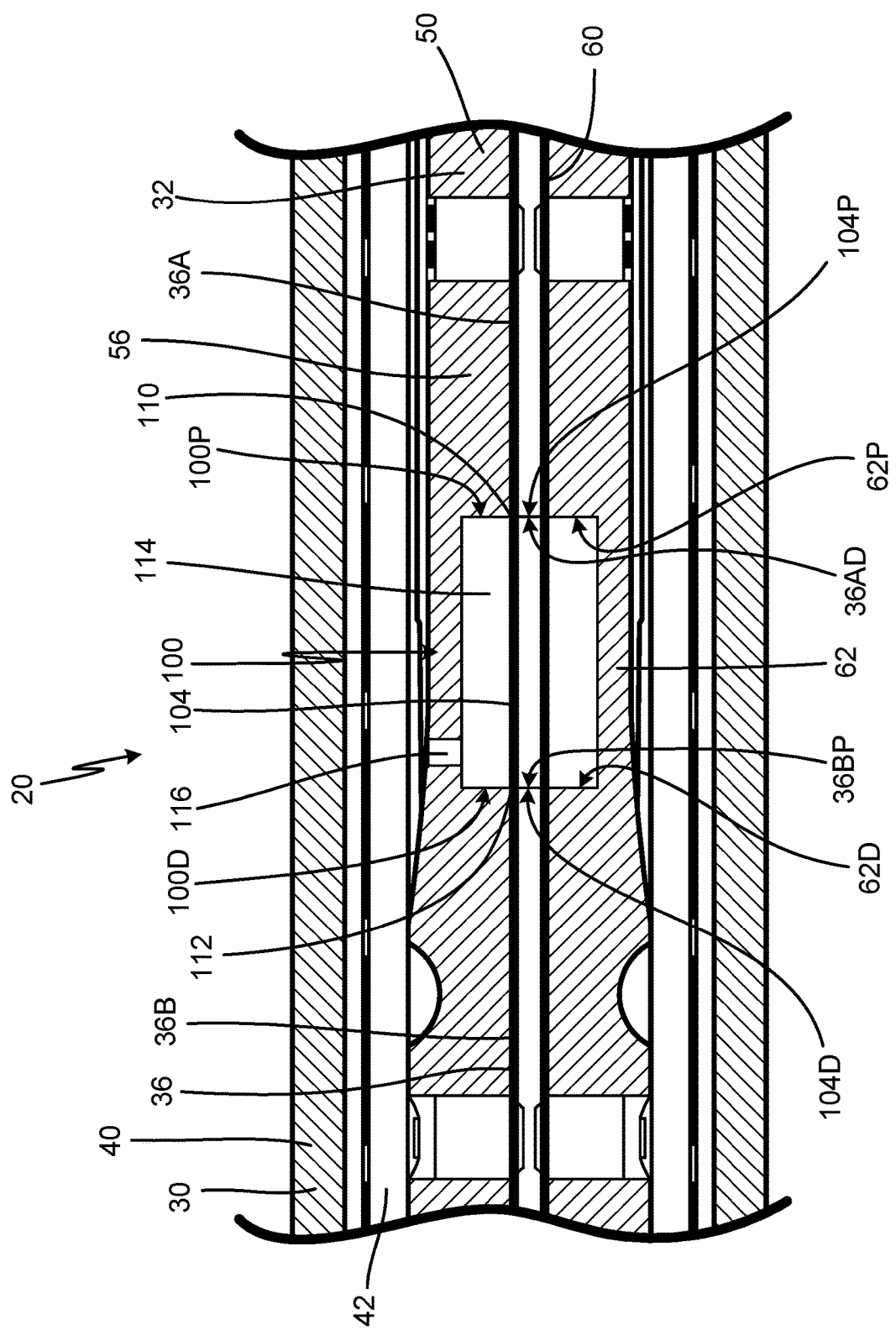
FIG. 8 is a cross-sectional view of the restrictor where the needle slider of the needle system forms the housing of the restrictor.

FIGS. 7-8 show two ways in which restrictor 100 can be incorporated into needle system 20.

FIG. 7 is a cross-sectional view of restrictor 100 where housing 102 of restrictor 100 is positioned in needle slider 32 of needle system 20. Needle system 20 includes handle 30, needle slider 32, and needle 36. Handle 30 includes housing 40 and first bore 42. Needle slider 32 includes housing 50, shaft 56, second bore 60, and notch 62. Needle 36 includes first needle portion 36A and second needle portion 36B. Restrictor 100 includes housing 102 and flexible member 104. Housing 102 includes proximal port 110, distal port 112, cavity 114, and vent holes 116.

Needle system 20 is described above in reference to FIGS. 1A-5. Restrictor 100 is described above in reference to FIGS. 6A-6B. Restrictor 100 is positioned in-line with needle 36 in needle slider 32 of needle system 20. Specifically, restrictor 100 is positioned in needle slider 32 of needle system 20. Housing 102 of restrictor 100 is positioned in shaft 56 of needle slider 32 in the embodiment shown in FIG. 7.

Notch 62 is formed in needle slider 32 to fit housing 102 of restrictor 100. Notch 62 has proximal end 62P and distal end 62D. An outer diameter of housing 102 abuts an inner diameter of notch 62 in needle slider 32; proximal end 102P of housing 102 of restrictor 100 abuts proximal end 62P of notch 62 in needle slider 32; and distal end 102D of housing 102 of restrictor 100 abuts distal end 62D of notch 62 in needle slider 32. Vent hole 116 extends through housing 102 of restrictor 100 and needle slider 32 to connect cavity 114 to an ambient surrounding needle slider 32.

Housing 102 of restrictor 100 can be affixed to needle slider 32 using any suitable means. As a first example, housing 102 can be welded to needle slider 32. An outer diameter of housing 102 of restrictor 100 can be welded to an inner diameter of notch 62 of needle slider 32; proximal end 102P of housing 102 of restrictor 100 can be welded to proximal end 62P of notch 62 of needle slider 32; and distal end 102D of housing 102 of restrictor 100 can be welded to distal end 62D of notch 62 of needle slider 32. As a second example, housing 102 of restrictor 100 can be adhered to needle slider 32. An outer diameter of housing 102 of restrictor 100 can be adhered to an inner diameter of notch 62 of needle slider 32; proximal end 102P of housing 102 of restrictor 100 can be adhered to proximal end 62P of notch 62 of needle slider 32; and distal end 102D of housing 102 of restrictor 100 can be adhered to distal end 62D of notch 62 of needle slider 32. As a third example, housing 102 of restrictor 100 can be press fit into needle slider 32. An outer diameter of housing 102 of restrictor 100 can be slightly larger than an inner diameter of notch 62 of needle slider 32, and a length of housing 102 from proximal end 102P to distal end 102D can be slightly larger than a length of notch 62 from proximal end 62P to distal end 62D to press fit housing 102 of restrictor 100 in notch 62 of needle slider 32.

Securing housing 102 of restrictor 100 to needle slider 32 of needle system 20 secures restrictor 100 in needle system 20. Restrictor 100 will move with needle slider 32. Securing housing 102 of restrictor 100 to needle slider 32 of needle system 20 allows restrictor 100 to be assembled prior to securing restrictor 100 to needle system 20.

FIG. 8 is a cross-sectional view of restrictor 100 where needle slider 32 of needle system 20 forms housing 102 of restrictor 100. Needle system 20 includes handle 30, needle slider 32, and needle 36. Handle 30 includes housing 40 and first bore 42. Needle slider 32 includes housing 50, shaft 56, second bore 60, and notch 62. Needle 36 includes first needle portion 36A and second needle portion 36B. Restrictor 100 includes flexible member 104, proximal port 110, distal port 112, cavity 114, and vent holes 116.

Needle system 20 is described above in reference to FIGS. 1A-5. Restrictor 100 is described above in reference to FIGS. 6A-6B. Restrictor 100 is positioned in-line with needle 36 in needle slider 32 of needle system 20. Specifically, restrictor 100 is positioned in needle slider 32 of needle system 20. Needle slider 32 forms the housing of restrictor 100 in the embodiment shown in FIG. 8.

Body 50 of needle slider 32 forms the housing of restrictor 100. Body 50 of needle slider 32 can be affixed to first needle portion 36A and second needle portion 36B using any suitable means, for example by overmolding. Notch 62 is formed in needle slider 32. Notch 62 has proximal end 62P and distal end 62D. Notch 62 defines cavity 114 of restrictor 100. Proximal port 110 is defined at proximal end 62P of notch 62, and distal port 112 is defined at distal end 62D of notch 62. Flexible member 104 extends from proximal port 110 to distal port 112, and thus extends from proximal end 62P of notch 62 to distal end 62D of notch 62. Vent hole 116 extends through needle slider 32 to connected cavity 114 of restrictor 100 to an ambient surrounding needle slider 32. Notch 62 is formed in shaft 56 of needle slider 32 in the embodiment shown in FIG. 8.

Forming a housing of restrictor 100 with needle slider 32 allows needle system 20 to be built with fewer parts. This reduces assembly time and the cost to manufacture needle system 20. Flexible member 104 of restrictor 100 can extend through notch 62 in needle slider 32 and a difference in a pressure in a lumen of flexible member 104 and a pressure in cavity 114 of restrictor 100 can cause flexible member 104 to deform. In this way, restrictor 100 operates the same, regardless of whether restrictor 100 has a separate housing or needle slider 32 forms the housing of restrictor 100.

FIGS. 9-12B show restrictors 200, 300, 400, and 500, which illustrate various means of attaching the flexible member of the restrictor to needle 36.

Figure 9:
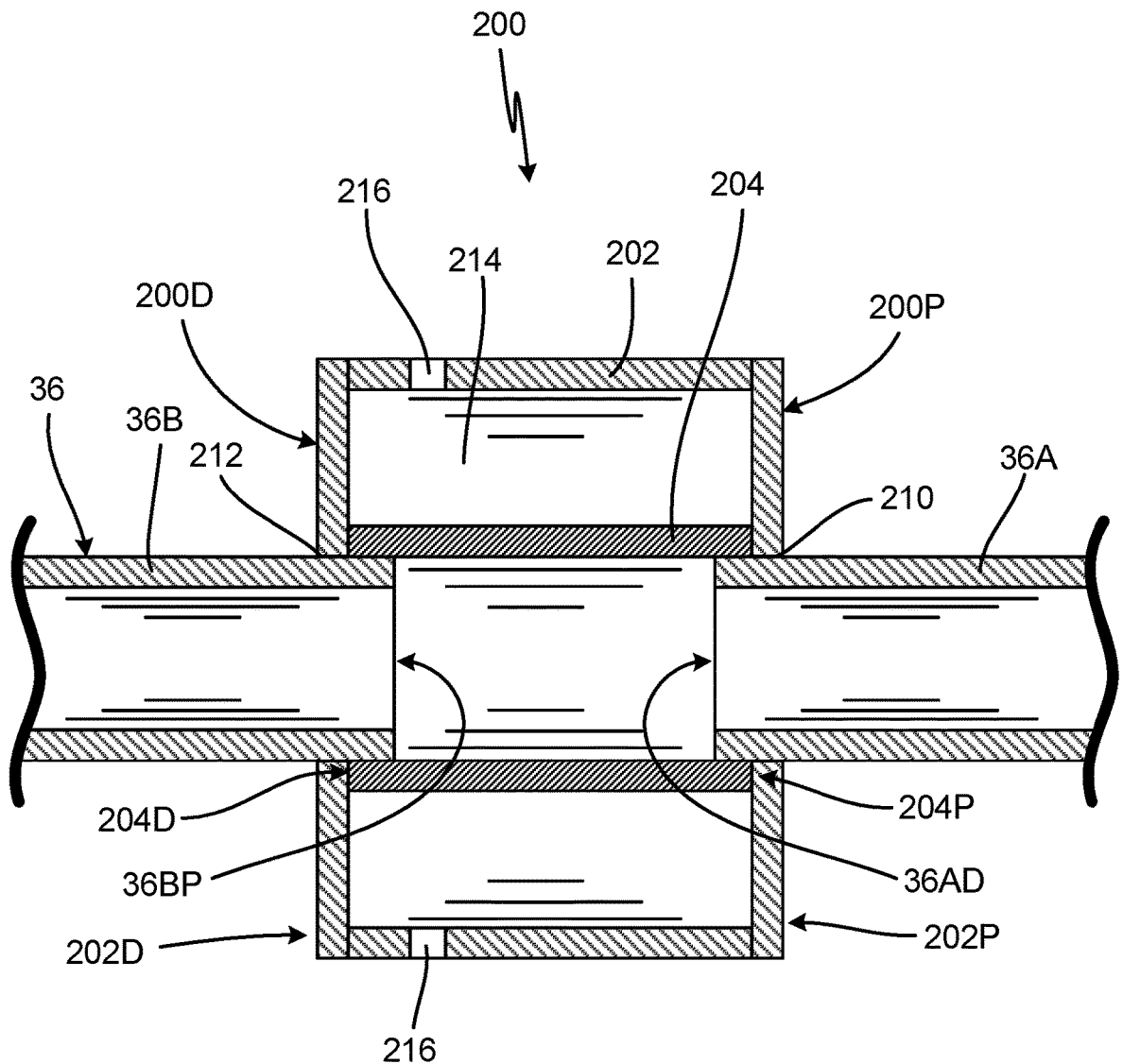
FIG. 9 is a cross-sectional view of the restrictor where a flexible member overlaps a needle.

Restrictor 200 (FIG. 9)

FIG. 9 is a cross-sectional view of restrictor 200 where flexible member 204 overlaps needle 36. FIG. 9 shows restrictor 200 in-line with needle 36. Needle 36 includes first needle portion 36A and second needle portion 36B. Restrictor 200 includes housing 202 and flexible member 204. Housing 202 includes proximal port 210, distal port 212, cavity 214, and vent holes 216.

Restrictor 200 has the same general structure and design as restrictor 100 described above in reference to FIGS. 6A-6B. Restrictor 200 shows a first means of attaching flexible member 204 to needle 36. Restrictor 200 has flexible member 204 that overlaps needle 36. Proximal end 204P of flexible member 204 overlaps distal end 36AD of first needle portion 36A, and distal end 204D of flexible member 204 overlaps proximal end 36BP of second needle portion 36B. Flexible member 204 overlaps needle 36 to hold flexible member 204 in-line with needle 36.

Flexible member 204 can be secured to needle 36 using any suitable means. As a first example, flexible member 204 can have an inner diameter that is the same size as or slightly smaller than an outer diameter of needle 36. Flexible member 204 can be stretched over needle 36 and will be held in place on needle 36 due to the tight fit between flexible member 204 and needle 36. An inner diameter of proximal end 204P of flexible member 204 will be secured to an outer diameter of distal end 36AD of first needle portion 36A, and an inner diameter of distal end 204D of flexible member 204 will be secured to an outer diameter of proximal end 36BP of second needle portion 36B. As a second example, flexible member 204 can be adhered to needle 36. An inner diameter of proximal end 204P of flexible member 204 can be adhered to an outer diameter of distal end 36AD of first needle portion 36A, and an inner diameter of distal end 204D of flexible member 204 can be adhered to an outer diameter of proximal end 36BP of second needle portion 36B. As a third example, flexible member 204 can be a shrink-wrap tube that is shrunk over needle 36. Proximal end 204P of flexible member 204 can be shrunk wrapped over distal end 36AD of first needle portion 36A, and distal end 204D of flexible member 204 can be shrunk wrapper over proximal end 36BP of second needle portion 36B.

The first means of attaching flexible member 204 of restrictor 200 to needle 36 shown in FIG. 9 allows a vacuum to be formed in a lumen of needle 36 and a lumen of flexible member 204. When a vacuum is formed, flexible member 204 can deform inwards, as shown in FIG. 6B above. In its deformed state, flexible member 204 will prevent biological material from moving through restrictor 200.

Figure 10:
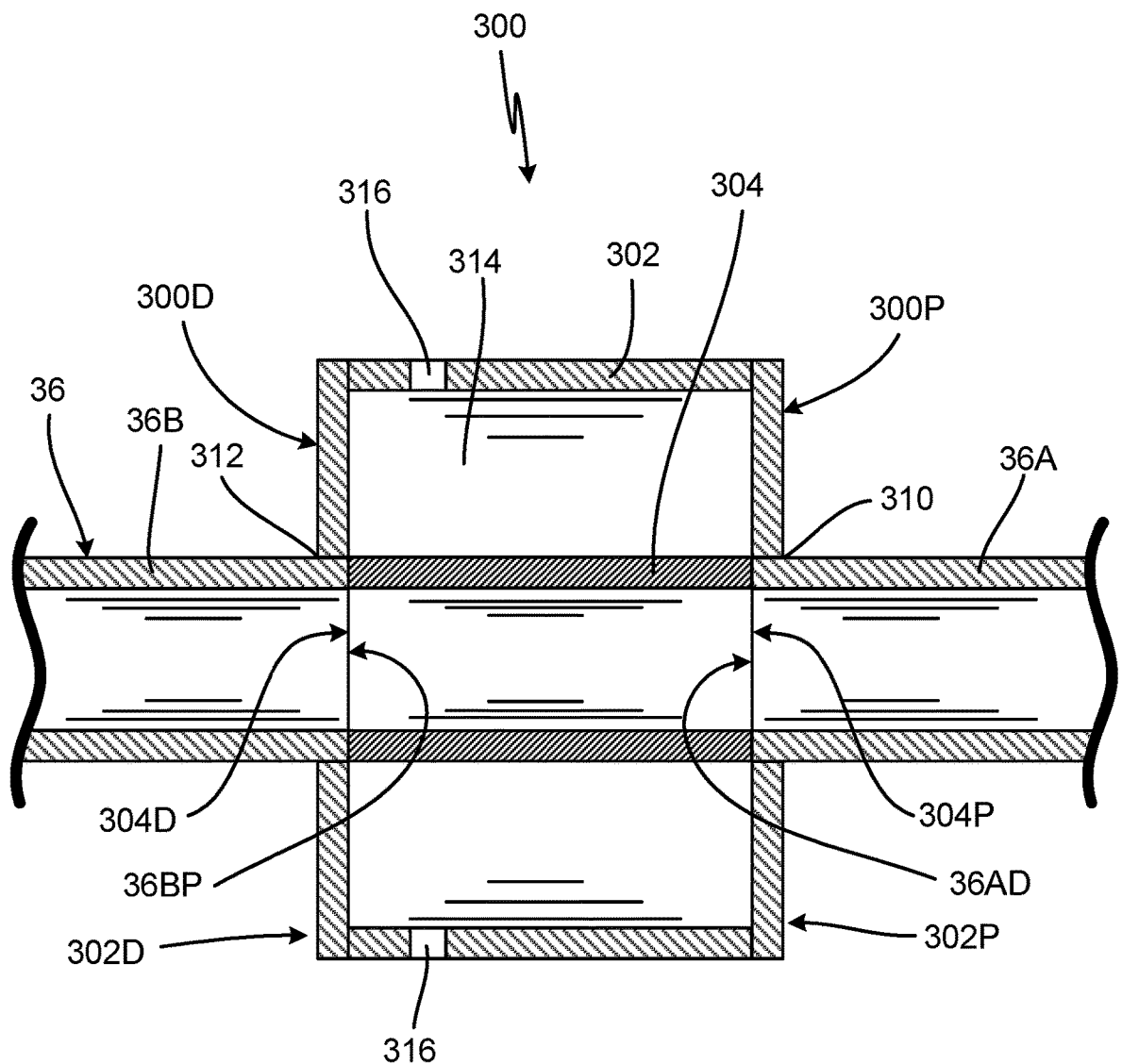
FIG. 10 is a cross-sectional view of the restrictor where the flexible member abuts the needle.

Restrictor 300 (FIG. 10)

FIG. 10 is a cross-sectional view of restrictor 300 where flexible member 304 abuts needle 36. FIG. 10 shows restrictor 300 in-line with needle 36. Needle 36 includes first needle portion 36A and second needle portion 36B. Restrictor 300 includes housing 302 and flexible member 304. Housing 302 includes proximal port 310, distal port 312, cavity 314, and vent holes 316.

Restrictor 300 has the same general structure and design as restrictor 100 described above in reference to FIGS. 6A-6B. Restrictor 300 shows a second means of attaching flexible member 304 to needle 36. Restrictor 300 has flexible member 304 that abuts needle 36. Proximal end 304P of flexible member 304 abuts distal end 36AD of first needle portion 36A, and distal end 304D of flexible member 304 abuts proximal end 36BP of second needle portion 36B. Flexible member 304 abuts needle 36 to hold flexible member 304 in-line with needle 36.

Flexible member 304 can be affixed to needle 36 using any suitable means. As a first example, flexible member 304 is secured to needle 36 with butt welds. Proximal end 304P of flexible member 304 can be secured to distal end 36AD of first needle portion 36A with a butt weld, and distal end 304D of flexible member 304 can be secured to proximal end 36BP of second needle portion 36B with a butt weld. As a second example, flexible member 304 is secured to needle 36 with butt adhesive joints. Proximal end 304P of flexible member 304 can be secured to distal end 36AD of first needle portion 36A with a butt adhesive joint, and distal end 304D of flexible member 304 can be secured to proximal end 36BP of second needle portion 36B with a butt adhesive joint.

The second means of attaching flexible member 304 of restrictor 300 to needle 36 shown in FIG. 10 allows a vacuum to be formed in a lumen of needle 36 and a lumen of flexible member 304. When a vacuum is formed, flexible member 304 can deform inwards, as shown in FIG. 6B above. In its deformed state, flexible member 304 will prevent biological material from moving through restrictor 300.

Figure 11A:
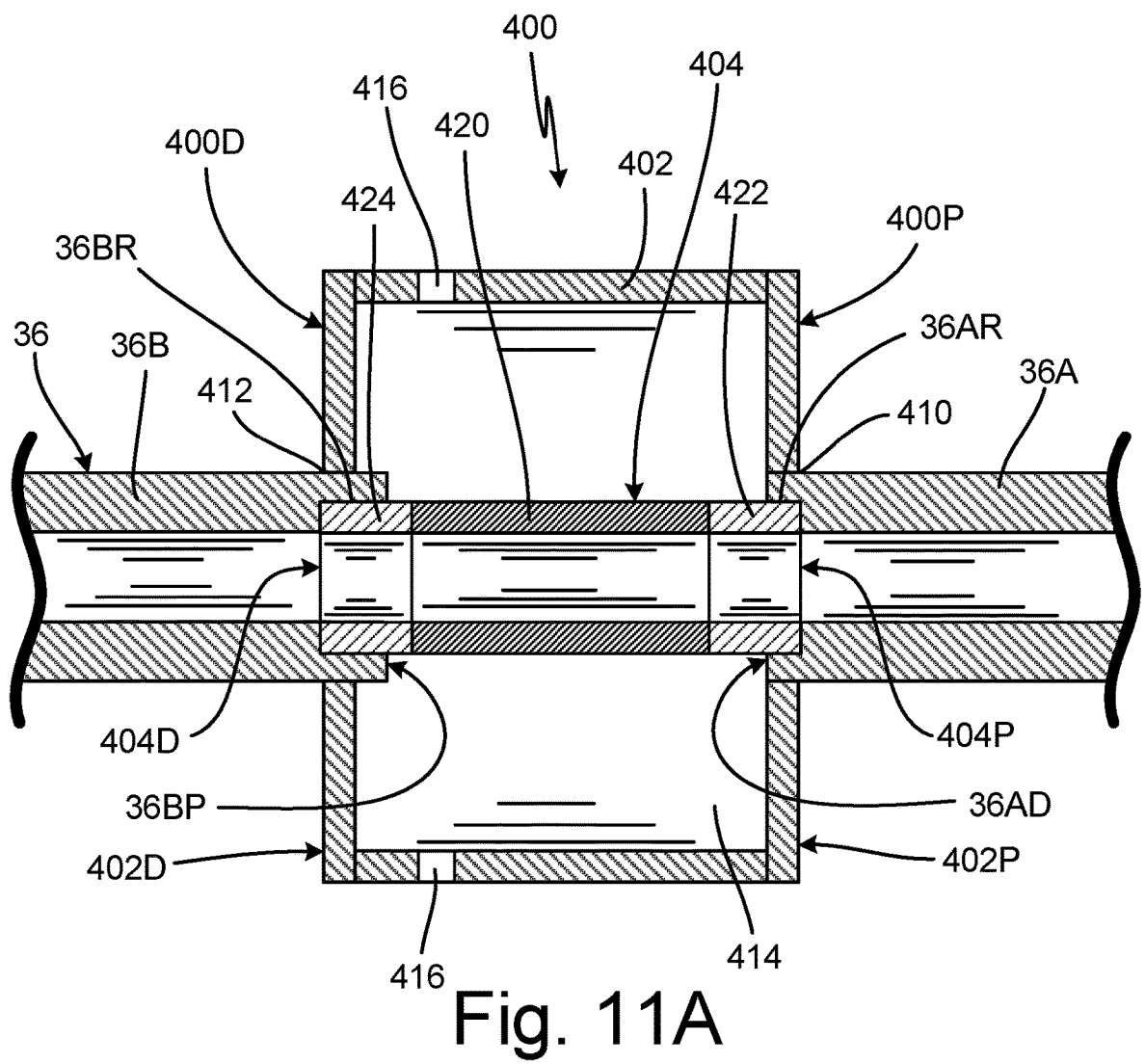
FIG. 11A is a cross-sectional view of the restrictor where the flexible member has rigid ends positioned in relief cuts in the needle.
Figure 11B:
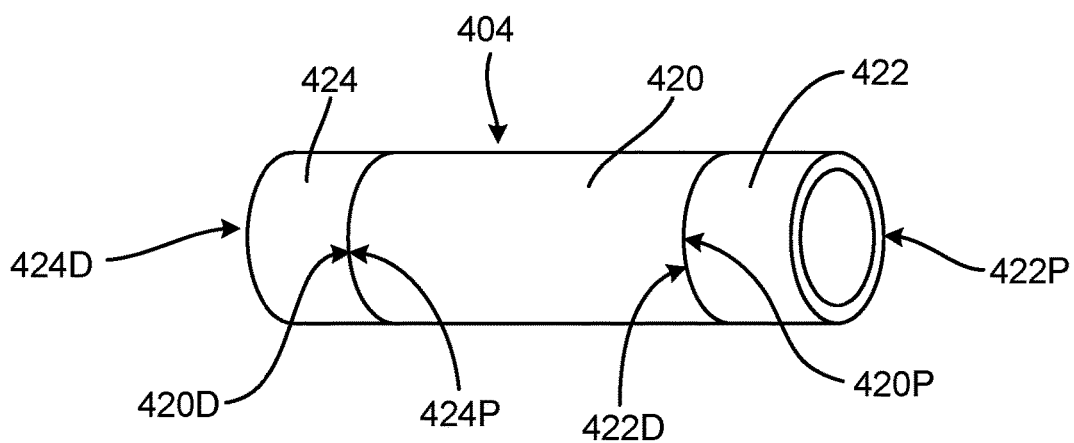
FIG. 11B is a perspective view of the flexible member with rigid ends.

Restrictor 400 (FIGS. 11A-11B)

FIG. 11A is a cross-sectional view of restrictor 400 where flexible member 404 has rigid ends 422 and 424 positioned in relief cuts 36AR and 36AB in needle 36. FIG. 11B is a perspective view of flexible member 404 with rigid ends 422 and 424. FIG. 11A shows restrictor 400 in-line with needle 36. Needle 36 includes first needle portion 36A, second needle portion 36B, first relief cut 36AR, and second relief cut 36BR. Restrictor 400 includes housing 402 and flexible member 404. Housing 402 includes proximal port 410, distal port 412, cavity 414, and vent holes 416. Flexible member 404 includes flexible portion 420, first rigid end 422, and second rigid end 424.

Restrictor 400 has the same general structure and design as restrictor 100 described above in reference to FIGS. 6A-6B. Restrictor 400 shows a third means of attaching flexible member 404 to needle 36. Needle 36 has first needle portion 36A with first relief cut 36AR on distal end 36AD and second needle portion 36B with second relief cut 36BR on proximal end 36BP. First relief cut 36AR and second relief cut 36BR are cut into needle 36 so that an inner diameter of needle 36 is smaller than an inner diameter of first relief cut 36AR and second relief cut 36BR.

Restrictor 400 has flexible member 404 that has flexible portion 420, first rigid end 422, and second rigid end 424. Flexible portion 420 has proximal end 420P and distal end 420D; first rigid end 422 has proximal end 422P and distal end 422D; and rigid end 424 has proximal end 424P and distal end 424D. Proximal end 420P of flexible portion 420 abuts and is connected to distal end 422D of first rigid end 422, and distal end 420D of flexible portion 420 abuts and is connected to proximal end 424P of second rigid end 424. Flexible portion 420, first rigid end 422, and second rigid end 424 form flexile member 404.

Flexible member 404 is positioned in needle 36 to hold flexible member 404 in-line with needle 36. First rigid portion 422 of flexile member 404 is positioned in first relief cut 36AR of first needle portion 36A and second rigid portion 424 of flexible member 404 is positioned in second relief cut 36BR of second needle portion 36B. An outer diameter of first rigid portion 422 of flexible member 404 abuts an inner diameter of first relief cut 36AR of first needle portion 36A, and an outer diameter of second rigid portion 424 of flexible member 404 abuts an inner diameter of second relief cut 36BR of second needle portion 36B. An inner diameter of flexible member 404 is the same as an inner diameter of needle 36.

Flexible member 404 can be secured to needle 36 using any suitable means. As a first example, flexible member 404 is secured to needle 36 by snapping it into needle 36. Rigid end 422 of flexible member 404 is snapped into first relief cut 36AR of first needle portion 36A, and rigid end 424 of flexible member 404 is snapped into second relief cut 36BR of second needle portion 36B. As a second example, flexible member 404 is secured to needle 36 by adhering it to needle 36. An outer diameter of rigid member 422 of flexible member 404 is adhered to an inner diameter of relief cut 36AR of first needle portion 36A, and an outer diameter of rigid member 424 of flexible member 404 is adhered to an inner diameter of relief cut 36AR of second needle portion 36B. As a third example, flexible member 404 is secured to needle 36 by press fitting or stretch fitting it to needle 36. An outer diameter of rigid member 422 of flexible member 404 and an outer diameter of rigid member 424 of flexible member 404 are sized to be slightly larger than an inner diameter of relief cut 36AR of first needle portion 36A and an inner diameter of relief cut 36BR of second needle portion 36B. When flexible member 404 is position in needle 36, the outer diameter of rigid member 422 of flexible member 404 will be press fit in the inner diameter of relief cut 36AR of first needle portion 36A and the outer diameter of rigid member 424 of flexible member 404 will be press fit in the inner diameter of relief cut 36BR of second needle portion 36B.

The third means of attaching flexible member 404 of restrictor 400 to needle 36 shown in FIGS. 11A-11B allows a vacuum to be formed in a lumen of needle 36 and a lumen of flexible member 404. When a vacuum is formed, flexible member 404 can deform inwards, as shown in FIG. 6B above. In its deformed state, flexible member 404 will prevent biological material from moving through restrictor 400.

Figure 12A:
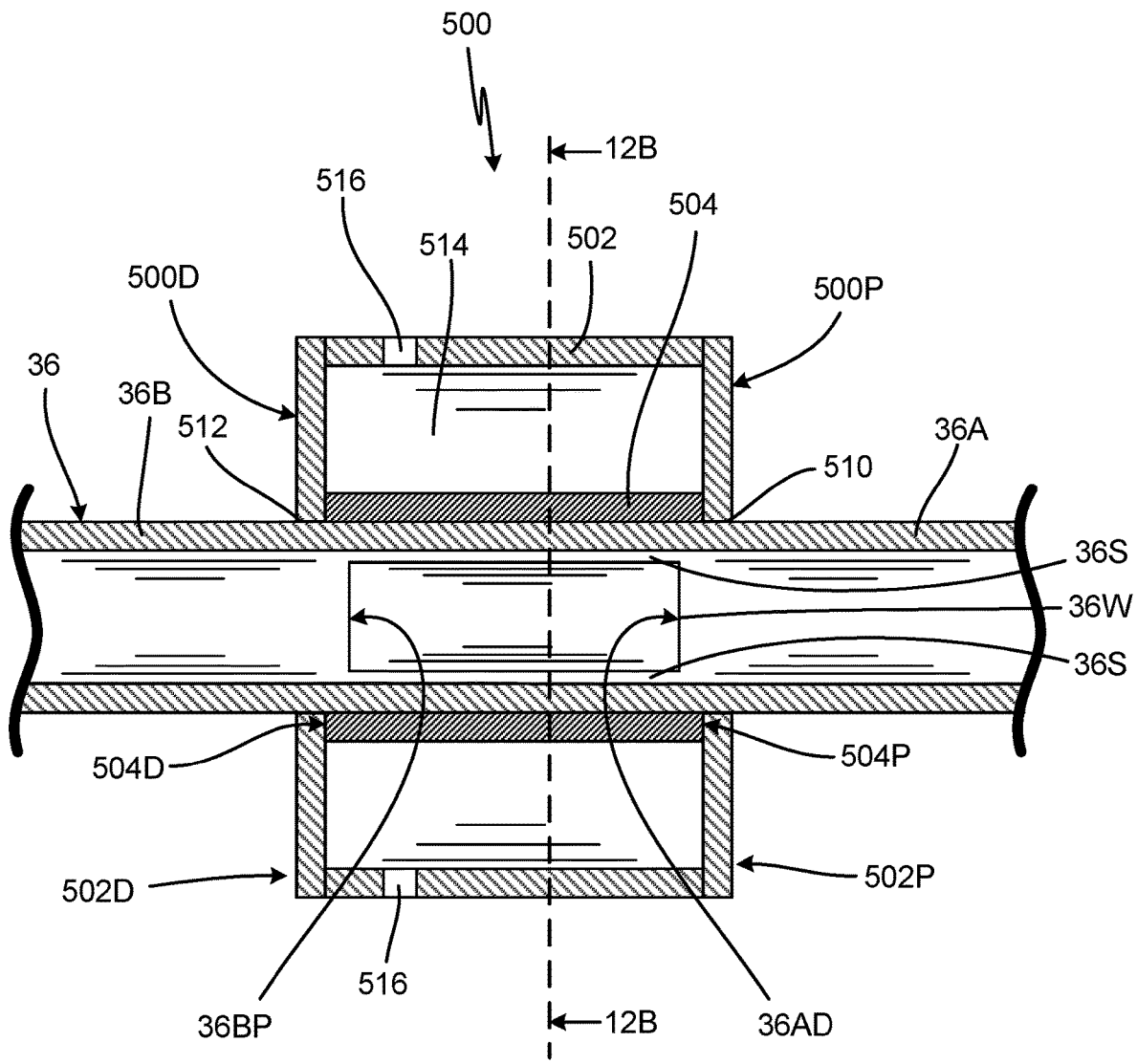
FIG. 12A is a cross-sectional view of the restrictor where the flexible member is positioned around struts in the needle.
Figure 12B:
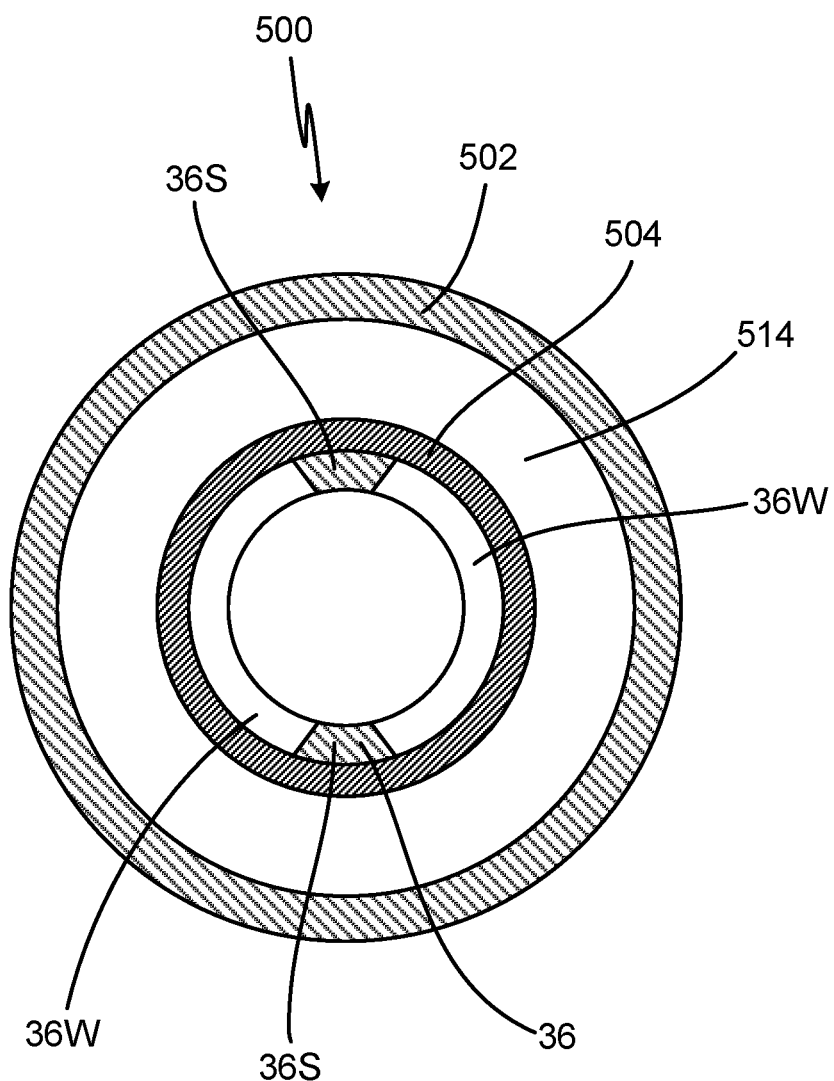
FIG. 12B is a cross-sectional view of the restrictor of FIG. 12A taken along line 12B-12B of FIG. 12A.

Restrictor 500 (FIGS. 12A-12B)

FIG. 12A is a cross-sectional view of restrictor 500 where flexible member 504 is positioned around struts 36S in needle 36. FIG. 12B is a cross-sectional view of restrictor 504 taken along line 12B-12B of FIG. 12A. FIG. 12A shows restrictor 500 in-line with needle 36. Needle 36 includes first needle portion 36A, second needle portion 36B, struts 36S, and windows 36W. Restrictor 500 includes housing 502 and flexible member 504. Housing 502 includes proximal port 510, distal port 512, cavity 514, and vent holes 516.

Restrictor 500 has the same general structure and design as restrictor 100 described above in reference to FIGS. 6A-6B. Restrictor 500 shows a fourth means of attaching flexible member 504 to needle 36. Needle 36 has struts 36S that connect first needle portion 36A to second needle portion 36B. Struts 36S extend from distal end 36AD of first needle portion 36A to proximal end 36BP of second needle portion 36B. Struts 36S are integrally formed with first needle portion 36A and second needle portion 36B. Windows 36W are openings in needle 36. Windows 36W are defined by distal end 36AD of first needle portion 36A, proximal end 36BP of second needle portion 36B, and struts 36S. In the embodiment shown in FIGS. 12A-12B, needle 36 has two struts 36S and two windows 36W. Needle 36 can have any suitable number of struts 36S and windows 36W in alternate embodiments.

Restrictor 500 has flexible member 504 that is positioned around needle 36. An inner diameter of flexible member 504 sits around an outer diameter of needle 36. Flexible member 504 extends across struts 36S and windows 36W of needle 36. Proximal end 104P of flexible member 104 extends past distal end 36AD of first needle portion 36A, and distal end 104D of flexible member 104 extends past proximal end 36BP of second needle portion 36B. A seal is formed between an inner diameter of proximal end 104P of flexible member 104 and an outer diameter of first needle portion 36A, and a seal is formed between an inner diameter of distal end 104D of flexible member 104 and an outer diameter of second needle portion 36B. Flexible member 104 can deform inwards through windows 36W in needle 36.

The fourth means of attaching flexible member 504 of restrictor 500 to needle 36 shown in FIGS. 12A-12B allows a vacuum to be formed in a lumen of needle 36 and a lumen of flexible member 504. When a vacuum is formed, flexible member 504 can deform inwards, as shown in FIG. 6B above. In its deformed state, flexible member 504 will prevent biological material from moving through restrictor 500.

As shown in FIGS. 9-12B, a flexible member of a restrictor can be adhered to needle 36 of needle system 20 using any suitable means. The means described in reference to FIGS. 9-12B are not limiting and other suitable means can be used.

Discussion of Possible Embodiments

The following are non-exclusive descriptions of possible embodiments of the present invention.

A needle system includes a handle, a needle slider partially positioned in the handle, and a needle connected to and extending away from the needle slider. A restrictor is disposed in the needle. The restrictor is configured to inhibit passage of a sample through the needle slider.

The needle system of the preceding paragraph can optionally include, additionally and/or alternatively, any one or more of the following features, configurations and/or additional components:

The restrictor permits fluid flow through the restrictor, and inhibits solid material from moving into the restrictor.

The restrictor includes a hollow housing with a proximal end having a proximal port and a distal end having a distal port, and a flexible member extending from the proximal port to the distal port of the hollow housing.

The flexible member is configured to deform when a vacuum is applied to the needle.

The housing is positioned around the needle.

An inner diameter of the proximal port of the hollow housing is welded to an outer diameter of a distal end of a first needle portion, and an inner diameter of the distal port of the hollow housing is welded to an outer diameter of a proximal end of a second needle portion.

The housing is secured in a notch in the needle slider.

The needle slider forms the hollow housing of the restrictor and a notch in the needle slider defines a cavity in the hollow housing.

The flexible member is coaxial with the needle.

The flexible member of the restrictor is made of an elastic polymer.

The hollow housing is made of a rigid material.

The needle system further includes a vent hole extending through the hollow housing.

The needle system further includes a cavity defined in the hollow housing.

A proximal end of the flexible member overlaps a distal end of a first needle portion and a distal end of the flexible member overlaps a proximal end of a second needle portion.

An inner diameter of the flexible member is slightly smaller than an outer diameter of the needle so that the flexible member is press fit to the needle.

An inner diameter of the flexible member is adhered to the outer diameter of the needle.

The flexible member is shrunk wrapped to the needle.

A proximal end of the flexible member abuts a distal end of a first needle portion and a distal end of the flexible member abuts a proximal end of a second needle portion.

The flexible member is connected to the needle with a butt weld.

The flexible member is connected to the needle with a butt adhesive joint.

The flexible member has a flexible portion, a first rigid end, and a second rigid end.

The needle has a first relief cut into an inner diameter of a distal end of a first needle portion and a second relief cut into an inner diameter of a proximal end of a second needle portion.

The first rigid end of the flexible member is positioned in the first relief cut of the first needle portion and the second rigid end of the flexible member is positioned in the second relief cut of the second needle portion.

The first rigid end of the flexible member is snapped into the first relief cut of the first needle portion and the second rigid end of the flexible member is snapped into the second relief cut of the second needle portion.

An outer diameter of the first rigid end of the flexible member is adhered to an inner diameter of the first relief cut of the first needle portion and an outer diameter of the second rigid end of the flexible member is adhered to an inner diameter of the second relief cut of the second needle portion.

An outer diameter of the first rigid end of the flexible member and an outer diameter of the second rigid end of the flexible member are larger than an inner diameter of the first relief cut of the first needle portion and an inner diameter of the second relief cut of the first needle portion so that the flexible member is press fit to the needle.

A first needle portion is connected to a second needle portion with a strut.

A window is opened through the needle and is defined by the first needle portion, the second needle portion, and the strut.

The flexible member is positioned around the strut and window of the needle.

The needle slider includes an aspiration port on a proximal end of the needle slider, a shaft on a distal end of the needle slider, and a grip between the aspiration port and the shaft.

The restrictor is positioned in a portion of the needle held in the shaft of the needle slider.

The needle system further includes a syringe connected to the aspiration port of the needle slider.

The shaft of the needle slider is movable in the handle.

The needle system further includes a sheath connected to and extending away from the handle, wherein the needle is positioned in and movable in the sheath.

The needle system further includes a stylet extending through the needle.

A needle system includes a needle slider having an aspiration port on a proximal end of the needle slider, a needle connected to and extending away from the needle slider, and a syringe attached to the aspiration port of the needle slider. A restrictor is disposed in the needle. The restrictor is configured to deform and inhibit passage of a sample through the needle slider when a vacuum is drawn by the syringe.

The needle system of the preceding paragraph can optionally include, additionally and/or alternatively, any one or more of the following features, configurations and/or additional components:

The restrictor permits fluid flow through the restrictor, and inhibits solid material from moving into the restrictor.

The restrictor includes a hollow housing with a proximal end having a proximal port and a distal end having a distal port, and a flexible member extending from the proximal port to the distal port of the hollow housing.

The flexible member is configured to deform when a vacuum is applied to the needle.

The housing is positioned around the needle.

An inner diameter of the proximal port of the hollow housing is welded to an outer diameter of a distal end of a first needle portion, and an inner diameter of the distal port of the hollow housing is welded to an outer diameter of a proximal end of a second needle portion.

The housing is secured in a notch in the needle slider.

The needle slider forms the hollow housing of the restrictor and a notch in the needle slider defines a cavity in the hollow housing.

The flexible member is coaxial with the needle.

The flexible member of the restrictor is made of an elastic polymer.

The hollow housing is made of a rigid material.

The needle system further includes a vent hole extending through the hollow housing.

The needle system further includes a cavity defined in the hollow housing.

A proximal end of the flexible member overlaps a distal end of a first needle portion and a distal end of the flexible member overlaps a proximal end of a second needle portion.

An inner diameter of the flexible member is slightly smaller than an outer diameter of the needle so that the flexible member is press fit to the needle.

An inner diameter of the flexible member is adhered to the outer diameter of the needle.

The flexible member is shrunk wrapped to the needle.

A proximal end of the flexible member abuts a distal end of a first needle portion and a distal end of the flexible member abuts a proximal end of a second needle portion.

The flexible member is connected to the needle with a butt weld.

The flexible member is connected to the needle with a butt adhesive joint.

The flexible member has a flexible portion, a first rigid end, and a second rigid end.

The needle has a first relief cut into an inner diameter of a distal end of a first needle portion and a second relief cut into an inner diameter of a proximal end of a second needle portion.

The first rigid end of the flexible member is positioned in the first relief cut of the first needle portion and the second rigid end of the flexible member is positioned in the second relief cut of the second needle portion.

The first rigid end of the flexible member is snapped into the first relief cut of the first needle portion and the second rigid end of the flexible member is snapped into the second relief cut of the second needle portion.

An outer diameter of the first rigid end of the flexible member is adhered to an inner diameter of the first relief cut of the first needle portion and an outer diameter of the second rigid end of the flexible member is adhered to an inner diameter of the second relief cut of the second needle portion.

An outer diameter of the first rigid end of the flexible member and an outer diameter of the second rigid end of the flexible member are larger than an inner diameter of the first relief cut of the first needle portion and an inner diameter of the second relief cut of the first needle portion so that the flexible member is press fit to the needle.

A first needle portion is connected to a second needle portion with a strut.

A window is opened through the needle and is defined by the first needle portion, the second needle portion, and the strut.

The flexible member is positioned around the strut and window of the needle.

The needle slider further includes a shaft on a distal end of the needle slider, and a grip between the aspiration port and the shaft.

The restrictor is positioned in a portion of the needle held in the shaft of the needle slider.

The shaft of the needle slider is movable in the handle.

The needle system further includes a sheath connected to and extending away from the handle, wherein the needle is positioned in and movable in the sheath.

The needle system further includes a stylet extending through the needle.

A restrictor includes a hollow housing with a proximal end having a proximal port and a distal end having a distal port, and a flexible member extending from the proximal port to the distal port of the hollow housing. The housing is configured to be positioned around a needle. The flexible member is configured to deform when a vacuum is applied to the needle.

The restrictor of the preceding paragraph can optionally include, additionally and/or alternatively, any one or more of the following features, configurations and/or additional components:

The flexible member of the restrictor is made of an elastic polymer.

The hollow housing is made of a rigid material.

The restrictor is coaxial with the needle.

In a natural state, an inner diameter of the flexible member is the same as an inner diameter of the needle.

In a deformed state, an inner diameter of the flexible member is smaller than an inner diameter of the needle.

The restrictor further includes a cavity defined in the hollow housing surrounding the flexible member.

When a vacuum is applied to the needle, a pressure in the cavity is greater than a pressure in the needle, causing the flexible member to deform.

The restrictor further includes a vent hole extending through the housing.

The cavity maintains an atmospheric pressure by fluid communication through the vent hole.

The flexible member is in-line with the needle so that a proximal end and a distal end of the flexible member are connected to the needle.

A proximal end of the flexible member is connected to a distal end of a first needle portion of the needle.

A distal end of the flexible member is connected to a proximal end of a second needle portion of the needle.

A proximal end of the flexible member overlaps a distal end of a first needle portion and a distal end of the flexible member overlaps a proximal end of a second needle portion.

An inner surface of the flexible member is slightly smaller than an outer diameter of the needle so that the flexible member is stretch fit to the needle.

An inner diameter of the flexible member is adhered to the outer diameter of the needle.

The flexible member is shrunk to the needle.

A proximal end of the flexible member abuts a distal end of a first needle portion and a distal end of the flexible member abuts a proximal end of a second needle portion.

The flexible member is connected to the needle with a butt weld.

The flexible member is connected to the needle with a butt adhesive joint.

The flexible member has a flexible portion, a first rigid end, and a second rigid end.

The needle has a first relief cut into an inner diameter of a distal end of a first needle portion and a second relief cut into an inner diameter of a proximal end of a second needle portion.

The first rigid end of the flexible member is positioned in the first relief cut of the first needle portion and the second rigid end of the flexible member is positioned in the second relief cut of the second needle portion.

The first rigid end of the flexible member is snapped into the first relief cut of the first needle portion and the second rigid end of the flexible member is snapped into the second relief cut of the second needle portion.

An outer diameter of the first rigid end of the flexible member is adhered to an inner diameter of the first relief cut of the first needle portion and an outer diameter of the second rigid end of the flexible member is adhered to an inner diameter of the second relief cut of the second needle portion.

An outer diameter of the first rigid end of the flexible member and an outer diameter of the second rigid end of the flexible member are larger than an inner diameter of the first relief cut of the first needle portion and an inner diameter of the second relief cut of the first needle portion so that the flexible member is press fit to the needle.

A first needle portion is connected to a second needle portion with a strut.

A window is opened through the needle and is defined by the first needle portion, the second needle portion, and the strut.

The flexible member is positioned around the strut and window of the needle.

The restrictor further includes a vent hole extending through the housing.

A method includes advancing a needle of the needle system out of a sheath of the needle system and into a biological sample. The needle system further includes a handle and a needle slider partially positioned in the handle. The sheath is secured in the handle and the needle is secured in the needle slider and extends through the sheath. A syringe is connected to an aspiration port of the needle slider of the needle system. A vacuum is created in the needle system with the syringe. A restrictor that is positioned in-line with the needle deforms under the vacuum in the needle system. The biological sample is aspirated into the needle of the needle system. The biological sample is inhibited, with the restrictor, from moving into the syringe.

The method of the preceding paragraph can optionally include, additionally and/or alternatively, any one or more of the following features, configurations and/or additional components:

The method further includes removing a stylet from the needle system.

Aspirating the biological sample into the needle further includes moving the needle slider of the needle system to move the needle in the biological sample.

Inhibiting the biological sample from moving into the syringe further includes restricting the diameter of a flow path in the needle system with the restrictor.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A restrictor comprising:
- a hollow housing with a proximal end having a proximal port and a distal end having a distal port;
- a needle having a first needle portion extending from the proximal port of the housing and a second needle portion extending from the distal port of the housing, wherein the housing is configured to be positioned around the needle;
- a flexible member extending from the proximal port to the distal port of the hollow housing, wherein the flexible member is in-line with the needle so that a proximal end and a distal end of the flexible member are connected to the needle, and wherein the flexible member is configured to deform when a vacuum is applied to the needle; and
- a vent hole extending through the housing.

2. The restrictor of claim 1, wherein the hollow housing is made of a rigid material.

3. The restrictor of claim 1, wherein in a natural state, an inner diameter of the flexible member is the same as an inner diameter of the needle.

4. The restrictor of claim 1, wherein in a deformed state, an inner diameter of the flexible member is smaller than an inner diameter of the needle.

5. The restrictor of claim 1, and further comprising:
- a cavity defined in the hollow housing surrounding the flexible member.

6. The restrictor of claim 1, wherein a proximal end of the flexible member is connected to a distal end of the first needle portion of the needle, and wherein a distal end of the flexible member is connected to a proximal end of the second needle portion of the needle.

7. The restrictor of claim 1, wherein a proximal end of the flexible member overlaps a distal end of the first needle portion and a distal end of the flexible member overlaps a proximal end of the second needle portion.

8. The restrictor of claim 1, wherein a proximal end of the flexible member abuts a distal end of the first needle portion and a distal end of the flexible member abuts a proximal end of the second needle portion.

9. The restrictor of claim 1, wherein the flexible member has a flexible portion, a first rigid end, and a second rigid end.

10. The restrictor of claim 9, wherein the needle has a first relief cut into an inner diameter of a distal end of the first needle portion and a second relief cut into an inner diameter of a proximal end of the second needle portion, and wherein the first rigid end of the flexible member is positioned in the first relief cut of the first needle portion and the second rigid end of the flexible member is positioned in the second relief cut of the second needle portion.

11. The restrictor of claim 1, wherein the first needle portion is connected to the second needle portion with a strut, wherein a window is opened through the needle and is defined by the first needle portion, the second needle portion, and the strut, and wherein the flexible member is positioned around the struts and window of the needle.

12. A needle system comprising:
- a handle;
- a needle slider partially positioned in the handle;
- a needle connected to and extending away from the needle slider; and
- a restrictor disposed in the needle, the restrictor being configured to inhibit passage of a sample through the needle slider, wherein the restrictor comprises:
  - a hollow housing with a proximal end having a proximal port and a distal end having a distal port; and
  - a flexible member extending from the proximal port to the distal port of the hollow housing;
  - wherein the needle slider forms the hollow housing of the restrictor and a notch in the needle slider defines a cavity in the hollow housing.

13. The needle system of claim 12, wherein the flexible member is configured to deform when a vacuum is applied to the needle.

14. The needle system of claim 12, wherein the needle slider comprises:
- an aspiration port on a proximal end of the needle slider; and
- a shaft on a distal end of the needle slider.

15. The needle system of claim 14, wherein the restrictor is positioned in a portion of the needle held in the shaft of the needle slider.

16. The needle system of claim 12, and further comprising:
- a sheath connected to and extending away from the handle, wherein the needle is positioned in and movable in the sheath.

17. A method comprising:
- advancing a needle of a needle system out of a sheath of the needle system and into a biological sample, wherein the needle system further includes a handle and a needle slider partially positioned in the handle, wherein the sheath is secured in the handle and the needle is secured in the needle slider and extends through the sheath;
- connecting a syringe to an aspiration port of the needle slider of the needle system;
- creating a vacuum in the needle system with the syringe, wherein a restrictor that is positioned in-line with the needle deforms under the vacuum in the needle system, the restrictor including one or more vent holes that provide fluid communication between an internal cavity of the restrictor and an ambient surrounding the restrictor;

aspirating the biological sample into the needle of the needle system; and inhibiting, with the restrictor, the biological sample from moving into the syringe.

18. The method of claim 17, wherein inhibiting the biological sample from moving into the syringe further comprises:

restricting a diameter of a flow path in the needle system with the restrictor.

19. A restrictor comprising:

a needle;

a hollow housing with a proximal end having a proximal port and a distal end having a distal port, the housing configured to be positioned around the needle; and a flexible member extending from the proximal port to the distal port of the hollow housing;

wherein the flexible member is in-line with the needle so that a proximal end of the flexible member is connected to a distal end of a first needle portion of the needle and a distal end of the flexible member is connected to a proximal end of a second needle portion of the needle; and wherein the flexible member is configured to deform when a vacuum is applied to the needle.

20. A restrictor comprising:

a needle;

a hollow housing with a proximal end having a proximal port and a distal end having a distal port, the housing configured to be positioned around the needle; and a flexible member extending from the proximal port to the distal port of the hollow housing;

wherein the flexible member is in-line with the needle so that a proximal end and a distal end of the flexible member are connected to the needle;

wherein a first needle portion is connected to a second needle portion with a strut, wherein a window is opened through the needle and is defined by the first needle portion, the second needle portion, and the strut, and wherein the flexible member is positioned around the struts and window of the needle; and wherein the flexible member is configured to deform when a vacuum is applied to the needle.

* * * * *